United States Patent
Estes

(10) Patent No.: US 10,449,294 B1
(45) Date of Patent: Oct. 22, 2019

(54) OPERATING AN INFUSION PUMP SYSTEM

(71) Applicant: Bigfoot Biomedical, Inc., Milpitas, CA (US)

(72) Inventor: Mark Estes, Milpitas, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 781 days.

(21) Appl. No.: 14/988,697

(22) Filed: Jan. 5, 2016

(51) Int. Cl.
*A61M 5/172* (2006.01)
*A61M 5/142* (2006.01)
*A61M 5/14* (2006.01)
*A61M 5/145* (2006.01)

(52) U.S. Cl.
CPC ........ *A61M 5/1723* (2013.01); *A61M 5/1413* (2013.01); *A61M 5/1452* (2013.01); *A61M 5/14244* (2013.01); *A61M 2205/3576* (2013.01); *A61M 2205/502* (2013.01); *A61M 2230/005* (2013.01); *A61M 2230/201* (2013.01)

(58) Field of Classification Search
CPC ............ A61M 5/1413; A61M 5/14244; A61M 5/1723; A61M 2005/14208; A61M 2005/14268; A61M 2205/505; A61M 2230/005; A61M 2230/201
See application file for complete search history.

(56) References Cited

U.S. PATENT DOCUMENTS

| | | |
|---|---|---|
| 2,605,765 A | 8/1952 | Kollsman |
| 3,886,938 A | 6/1975 | Szabo et al. |
| 4,077,405 A | 3/1978 | Haerten et al. |
| 4,151,845 A | 5/1979 | Clemens |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,475,901 A | 10/1984 | Kraegen et al. |
| 4,493,704 A | 1/1985 | Beard et al. |

(Continued)

FOREIGN PATENT DOCUMENTS

| | | |
|---|---|---|
| CA | 2543545 | 5/2005 |
| DE | 196 27 619 | 1/1998 |
| DE | 102 36 669 | 2/2004 |

(Continued)

OTHER PUBLICATIONS

"Minimed Inc. Introduces 407C Infusion Pump for General Medication Use" [online]. Business Wire, AllBusiness.com, Aug. 10, 1999 [retrieved on Feb. 28, 2011]. Retrieved from the Internet: <URL: http://www.allbusiness.com/company-activities-management/product-management/6734565-1.html>.

(Continued)

*Primary Examiner* — Kami A Bosworth
(74) *Attorney, Agent, or Firm* — Fish & Richardson P.C.

(57) ABSTRACT

An infusion pump system can operate to control dispensation of medicine according to a closed-loop delivery mode and according to an open-loop delivery mode. In the closed-loop delivery mode, the system can determine user-specific settings. In the open-loop delivery mode, the system can determine insulin dosages for dispensation based at least in part on the user-specific settings that were determined during the closed-loop delivery mode.

11 Claims, 10 Drawing Sheets

(56) References Cited

U.S. PATENT DOCUMENTS

| | | |
|---|---|---|
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,822,715 A | 10/1998 | Worthington |
| 5,852,803 A | 12/1998 | Ashby, III et al. |
| 5,873,731 A | 2/1999 | Prendergast |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,126,595 A | 10/2000 | Amano |
| 6,156,014 A | 12/2000 | Petersen et al. |
| 6,171,276 B1 | 1/2001 | Lippe et al. |
| 6,231,540 B1 | 5/2001 | Smedegaard |
| 6,233,471 B1 | 5/2001 | Berner et al. |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,301 B1 | 4/2002 | Worthington et al. |
| 6,379,339 B1 | 4/2002 | Klitgaard et al. |
| 6,381,496 B1 | 4/2002 | Meadows et al. |
| 6,397,098 B1 | 5/2002 | Uber, III et al. |
| 6,404,098 B1 | 6/2002 | Kayama et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,212 B2 | 4/2003 | Galley |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,345 B1 | 5/2003 | Houben et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,572,545 B2 | 6/2003 | Knobbe et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,587,199 B1 | 7/2003 | Luu |
| 6,589,229 B1 | 7/2003 | Connelly et al. |
| 6,599,281 B1 | 7/2003 | Struys et al. |
| 6,605,067 B1 | 8/2003 | Larsen |
| 6,605,072 B2 | 8/2003 | Struys et al. |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B2 | 7/2005 | Whitehurst |
| 6,923,763 B1 | 8/2005 | Kovatchev et al. |
| 6,925,393 B1 | 8/2005 | Kalatz |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |

(56) References Cited

U.S. PATENT DOCUMENTS

| | | |
|---|---|---|
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,060,059 B2 | 6/2006 | Keith et al. |
| 7,066,910 B2 | 6/2006 | Bauhahn et al. |
| 7,104,972 B2 | 9/2006 | Møller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,179,226 B2 | 2/2007 | Crothall et al. |
| 7,204,823 B2 | 4/2007 | Estes et al. |
| 7,220,240 B2 | 5/2007 | Struys et al. |
| 7,232,423 B2 | 6/2007 | Mernoe et al. |
| 7,267,665 B2 | 9/2007 | Steil et al. |
| 7,278,983 B2 | 10/2007 | Ireland et al. |
| 7,291,107 B2 | 11/2007 | Hellwig et al. |
| 7,354,420 B2 | 4/2008 | Steil et al. |
| 7,402,153 B2 | 7/2008 | Steil et al. |
| 7,404,796 B2 | 7/2008 | Ginsberg |
| 7,429,255 B2 | 9/2008 | Thompson |
| 7,491,187 B2 | 2/2009 | Van Den Berghe et al. |
| 7,547,281 B2 | 6/2009 | Hayes et al. |
| 7,569,030 B2 | 8/2009 | Lebel et al. |
| 7,570,980 B2 | 8/2009 | Ginsberg |
| 7,591,801 B2 | 9/2009 | Brauker et al. |
| 7,651,845 B2 | 1/2010 | Doyle, III et al. |
| 7,670,288 B2 | 3/2010 | Sher |
| 7,704,226 B2 | 4/2010 | Mueller, Jr. et al. |
| 7,734,323 B2 | 6/2010 | Blomquist et al. |
| 7,785,313 B2 | 8/2010 | Mastrototaro |
| 7,806,853 B2 | 10/2010 | Wittmann et al. |
| 7,806,854 B2 | 10/2010 | Damiano et al. |
| 7,806,886 B2 | 10/2010 | Kanderian, Jr. et al. |
| 7,815,602 B2 | 10/2010 | Mann et al. |
| 7,819,843 B2 | 10/2010 | Mann et al. |
| 7,850,641 B2 | 12/2010 | Lebel et al. |
| 7,879,026 B2 | 2/2011 | Estes et al. |
| 7,946,985 B2 | 5/2011 | Mastrototaro et al. |
| 7,959,598 B2 | 6/2011 | Estes |
| 7,967,812 B2 | 6/2011 | Jasperson et al. |
| 7,976,492 B2 | 7/2011 | Brauker et al. |
| 8,029,459 B2 | 10/2011 | Rush et al. |
| 8,062,249 B2 | 11/2011 | Wilinska et al. |
| 8,088,098 B2 | 1/2012 | Yodfat et al. |
| 8,105,268 B2 | 1/2012 | Lebel et al. |
| 8,114,023 B2 | 2/2012 | Ward et al. |
| 8,152,789 B2 | 4/2012 | Starkweather et al. |
| 8,206,296 B2 | 6/2012 | Jennewine |
| 8,206,350 B2 | 6/2012 | Mann et al. |
| 8,208,984 B2 | 6/2012 | Blomquist et al. |
| 8,226,556 B2 | 7/2012 | Hayes et al. |
| 8,246,540 B2 | 8/2012 | Ginsberg |
| 8,257,300 B2 | 9/2012 | Budiman et al. |
| 8,267,893 B2 | 9/2012 | Moberg et al. |
| 8,273,052 B2 | 9/2012 | Damiano et al. |
| 8,318,154 B2 | 11/2012 | Frost et al. |
| 8,348,844 B2 | 1/2013 | Kunjan et al. |
| 8,348,886 B2 | 1/2013 | Kanderian, Jr. et al. |
| 8,348,923 B2 | 1/2013 | Kanderian, Jr. et al. |
| 8,352,011 B2 | 1/2013 | Van Antwerp et al. |
| 8,417,311 B2 | 4/2013 | Rule |
| 8,439,834 B2 | 5/2013 | Schmelzeisen-Redeker et al. |
| 8,439,897 B2 | 5/2013 | Yodfat et al. |
| 8,454,576 B2 | 6/2013 | Mastrototaro et al. |
| 8,460,231 B2 | 6/2013 | Brauker et al. |
| 8,467,972 B2 | 6/2013 | Rush |
| 8,475,409 B2 | 7/2013 | Tsoukalis |
| 8,480,655 B2 | 7/2013 | Jasperson et al. |
| 8,548,544 B2 | 10/2013 | Kircher, Jr. et al. |
| 8,548,552 B2 | 10/2013 | Tsoukalis |
| 8,551,045 B2 | 10/2013 | Sie et al. |
| 8,560,082 B2 | 10/2013 | Wei |
| 8,560,131 B2 | 10/2013 | Haueter et al. |
| 8,562,558 B2 | 10/2013 | Kamath et al. |
| 8,562,587 B2 | 10/2013 | Kovatchev et al. |
| 8,568,713 B2 | 10/2013 | Frost et al. |
| 8,579,854 B2 | 11/2013 | Budiman et al. |
| 8,579,879 B2 | 11/2013 | Palerm et al. |
| 8,585,591 B2 | 11/2013 | Sloan et al. |
| 8,585,593 B2 | 11/2013 | Kovatchev et al. |
| 8,585,637 B2 | 11/2013 | Wilinska et al. |
| 8,585,638 B2 | 11/2013 | Blomquist |
| 8,597,274 B2 | 12/2013 | Sloan et al. |
| 8,615,366 B2 | 12/2013 | Galley et al. |
| 8,622,988 B2 | 1/2014 | Hayter |
| 8,679,016 B2 | 3/2014 | Mastrototaro et al. |
| 8,734,422 B2 | 3/2014 | Hayter |
| 8,690,820 B2 | 4/2014 | Cinar et al. |
| 8,694,115 B2 | 4/2014 | Goetz et al. |
| 8,706,691 B2 | 4/2014 | McDaniel et al. |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,428 B2 | 5/2014 | Blomquist |
| 8,747,315 B2 | 6/2014 | Brauker et al. |
| 8,762,070 B2 | 6/2014 | Doyle, III et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,784,364 B2 | 7/2014 | Kamen et al. |
| 8,784,369 B2 | 7/2014 | Starkweather et al. |
| 8,784,370 B2 | 7/2014 | Lebel et al. |
| 8,795,224 B2 | 8/2014 | Starkweather et al. |
| 8,795,252 B2 | 8/2014 | Hayter |
| 8,876,755 B2 | 11/2014 | Taub et al. |
| 8,882,741 B2 | 11/2014 | Brauker et al. |
| 8,903,501 B2 | 12/2014 | Perryman et al. |
| 8,919,180 B2 | 12/2014 | Gottlieb et al. |
| 8,920,401 B2 | 12/2014 | Brauker et al. |
| 8,926,585 B2 | 1/2015 | Brauker et al. |
| 8,945,094 B2 | 2/2015 | Nordh |
| 8,956,291 B2 | 2/2015 | Valk et al. |
| 8,956,321 B2 | 2/2015 | DeJournett |
| 8,977,504 B2 | 3/2015 | Hovorka |
| 8,992,475 B2 | 3/2015 | Mann et al. |
| 9,034,323 B2 | 5/2015 | Frost et al. |
| 9,050,413 B2 | 6/2015 | Brauker et al. |
| 9,056,165 B2 | 6/2015 | Steil et al. |
| 9,056,168 B2 | 6/2015 | Kircher, Jr. et al. |
| 9,089,305 B2 | 7/2015 | Hovorka |
| 9,149,233 B2 | 10/2015 | Kamath et al. |
| 9,155,843 B2 | 10/2015 | Brauker et al. |
| 9,247,901 B2 | 2/2016 | Kamath et al. |
| 9,320,471 B2 | 4/2016 | Hayes et al. |
| 9,333,298 B2 | 5/2016 | Kim et al. |
| 9,415,157 B2 | 8/2016 | Mann et al. |
| 9,474,855 B2 | 10/2016 | McCann et al. |
| 9,480,796 B2 | 11/2016 | Starkweather et al. |
| 9,486,172 B2 | 11/2016 | Cobelli et al. |
| 9,486,578 B2 | 11/2016 | Finan et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0016534 A1 | 2/2002 | Trepagnier et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0060753 A1 | 3/2003 | Starkweather et al. |
| 2003/0088238 A1 | 3/2003 | Poulsen et al. |
| 2003/0104982 A1 | 3/2003 | Flaherty |
| 2003/0130616 A1 | 3/2003 | Flaherty |
| 2003/0065308 A1 | 4/2003 | Lebel et al. |
| 2003/0208113 A1 | 5/2003 | Poulsen et al. |
| 2003/0114836 A1 | 6/2003 | Estes |
| 2003/0181852 A1 | 9/2003 | Mann et al. |

(56) References Cited

U.S. PATENT DOCUMENTS

| | | |
|---|---|---|
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0199825 A1 | 10/2003 | Flaherty |
| 2003/0212364 A1 | 11/2003 | Mann et al. |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0078028 A1 | 1/2004 | Flaherty et al. |
| 2004/0087894 A1 | 1/2004 | Shekalim |
| 2004/0064088 A1 | 4/2004 | Gorman et al. |
| 2004/0064096 A1 | 4/2004 | Flaherty et al. |
| 2004/0092865 A1 | 4/2004 | Gorman et al. |
| 2004/0092878 A1 | 4/2004 | Flaherty et al. |
| 2004/0116866 A1 | 4/2004 | Flaherty et al. |
| 2004/0127844 A1 | 5/2004 | Flaherty |
| 2004/0153032 A1 | 5/2004 | Flaherty et al. |
| 2004/0167464 A1 | 5/2004 | Flaherty |
| 2004/0171983 A1 | 6/2004 | Gorman et al. |
| 2004/0176720 A1 | 6/2004 | Gorman et al. |
| 2004/0176727 A1 | 7/2004 | Flaherty |
| 2004/0193025 A1 | 8/2004 | Garribotto et al. |
| 2004/0204673 A1 | 8/2004 | Ireland et al. |
| 2004/0220551 A1 | 9/2004 | Kipfer |
| 2004/0235446 A1 | 9/2004 | Shekalim |
| 2004/0220517 A1 | 11/2004 | Starkweather et al. |
| 2004/0260233 A1 | 12/2004 | Garibotto et al. |
| 2005/0021005 A1 | 1/2005 | Flaherty et al. |
| 2005/0021104 A1 | 1/2005 | DiLorenzo |
| 2005/0022274 A1 | 1/2005 | Campbell et al. |
| 2005/0090808 A1 | 1/2005 | Flaherty et al. |
| 2005/0160858 A1 | 1/2005 | Campbell et al. |
| 2005/0065465 A1 | 3/2005 | Lebel et al. |
| 2005/0065760 A1 | 3/2005 | Murtfeldt et al. |
| 2005/0095063 A1 | 5/2005 | Fathallah et al. |
| 2005/0171512 A1 | 8/2005 | Flaherty |
| 2005/0171513 A1 | 8/2005 | Mann et al. |
| 2005/0182366 A1 | 8/2005 | Flaherty |
| 2005/0192561 A1 | 8/2005 | Vogt et al. |
| 2005/0203461 A1 | 9/2005 | Flaherty et al. |
| 2005/0215982 A1 | 9/2005 | Flaherty et al. |
| 2005/0222645 A1 | 9/2005 | Malave et al. |
| 2005/0238507 A1 | 10/2005 | Malave et al. |
| 2005/0240544 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2005/0277890 A1 | 12/2005 | Stewart et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0173406 A1 | 8/2006 | Hayes et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0224109 A1 | 10/2006 | Steil et al. |
| 2006/0247581 A1 | 11/2006 | Pedersen et al. |
| 2007/0016127 A1 | 1/2007 | Staib et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0118405 A1 | 5/2007 | Campbell et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173761 A1 | 7/2007 | Kanderian, Jr. et al. |
| 2007/0179444 A1 | 8/2007 | Causey et al. |
| 2007/0219432 A1 | 9/2007 | Thompson |
| 2007/0282299 A1 | 12/2007 | Hellwig |
| 2008/0033357 A1 | 2/2008 | Mann et al. |
| 2008/0109050 A1 | 5/2008 | John |
| 2008/0125700 A1 | 5/2008 | Moberg et al. |
| 2008/0129535 A1 | 6/2008 | Thompson |
| 2008/0147004 A1 | 6/2008 | Mann et al. |
| 2008/0147050 A1 | 6/2008 | Mann et al. |
| 2008/0172027 A1 | 7/2008 | Blomquist |
| 2008/0177165 A1 | 7/2008 | Blomquist et al. |
| 2008/0183060 A1 | 7/2008 | Steil et al. |
| 2008/0188796 A1 | 8/2008 | Steil et al. |
| 2008/0201325 A1 | 8/2008 | Doniger et al. |
| 2008/0269714 A1* | 10/2008 | Mastrototaro ..... A61B 5/14532 604/504 |
| 2008/0269723 A1 | 10/2008 | Mastrototaro et al. |
| 2008/0275384 A1 | 11/2008 | Mastrototaro |
| 2008/0294094 A1 | 11/2008 | Mhatre et al. |
| 2008/0294142 A1 | 11/2008 | Patel et al. |
| 2008/0306434 A1 | 12/2008 | Dobbles et al. |
| 2008/0306444 A1 | 12/2008 | Brister |
| 2008/0312512 A1 | 12/2008 | Brukalo et al. |
| 2009/0043291 A1 | 2/2009 | Thompson |
| 2009/0048584 A1 | 2/2009 | Thompson |
| 2009/0069784 A1 | 3/2009 | Estes et al. |
| 2009/0069787 A1 | 3/2009 | Estes et al. |
| 2009/0099507 A1 | 4/2009 | Koops |
| 2009/0118664 A1 | 5/2009 | Estes et al. |
| 2009/0143916 A1 | 6/2009 | Boll et al. |
| 2009/0149728 A1 | 6/2009 | Van Antwerp et al. |
| 2009/0192722 A1 | 7/2009 | Shariati et al. |
| 2009/0105636 A1 | 8/2009 | Hayter et al. |
| 2009/0234213 A1 | 9/2009 | Hayes et al. |
| 2009/0264856 A1 | 10/2009 | Lebel et al. |
| 2010/0010329 A1 | 1/2010 | Taub et al. |
| 2010/0056992 A1 | 3/2010 | Hayter |
| 2010/0057040 A1 | 3/2010 | Hayter |
| 2010/0057041 A1 | 3/2010 | Hayter |
| 2010/0057042 A1 | 3/2010 | Hayter |
| 2010/0094251 A1 | 4/2010 | Estes |
| 2010/0121167 A1 | 5/2010 | McGarraugh |
| 2010/0165795 A1 | 7/2010 | Elder et al. |
| 2010/0168538 A1 | 7/2010 | Keenan et al. |
| 2010/0168820 A1 | 7/2010 | Maniak et al. |
| 2010/0174266 A1 | 7/2010 | Estes |
| 2010/0179409 A1 | 7/2010 | Kamath et al. |
| 2010/0228110 A1 | 9/2010 | Tsoukalis |
| 2010/0280441 A1 | 11/2010 | Wilinska et al. |
| 2010/0298765 A1 | 11/2010 | Budiman et al. |
| 2010/0324382 A1 | 12/2010 | Cantwell et al. |
| 2011/0015511 A1 | 1/2011 | Bousamra et al. |
| 2011/0034909 A1 | 2/2011 | Lebel et al. |
| 2011/0071464 A1 | 3/2011 | Palerm |
| 2011/0098637 A1 | 4/2011 | Hill |
| 2011/0106011 A1 | 5/2011 | Cinar et al. |
| 2011/0106050 A1* | 5/2011 | Yodfat ............. A61M 5/14248 604/504 |
| 2011/0112505 A1 | 5/2011 | Starkweather et al. |
| 2011/0112506 A1 | 5/2011 | Starkweather et al. |
| 2011/0118699 A1* | 5/2011 | Yodfat ............. A61M 5/14248 604/504 |
| 2011/0130716 A1 | 6/2011 | Estes et al. |
| 2011/0184380 A1 | 7/2011 | Starkweather et al. |
| 2011/0208155 A1 | 8/2011 | Palerm et al. |
| 2011/0313390 A1 | 12/2011 | Roy et al. |
| 2012/0010600 A1 | 1/2012 | Wilinska et al. |
| 2012/0046606 A1 | 2/2012 | Arefieg |
| 2012/0065894 A1 | 3/2012 | Tubb et al. |
| 2012/0078067 A1 | 3/2012 | Kovatchev et al. |
| 2012/0109113 A1 | 5/2012 | Lebel et al. |
| 2012/0123234 A1 | 5/2012 | Atlas et al. |
| 2012/0136336 A1 | 5/2012 | Mastrototaro et al. |
| 2012/0150556 A1 | 6/2012 | Galasso et al. |
| 2012/0172694 A1 | 7/2012 | Desborough et al. |
| 2012/0172802 A1 | 7/2012 | Blomquist |
| 2012/0197207 A1 | 8/2012 | Stefanski |
| 2012/0203467 A1 | 8/2012 | Kamath et al. |
| 2012/0209208 A1 | 8/2012 | Stefanski |
| 2012/0227737 A1 | 9/2012 | Mastrototaro et al. |
| 2012/0238853 A1 | 9/2012 | Arefieg |
| 2012/0245448 A1 | 9/2012 | Shariati et al. |

(56) References Cited

U.S. PATENT DOCUMENTS

| | | |
|---|---|---|
| 2012/0245556 A1 | 9/2012 | Kovatchev et al. |
| 2012/0245855 A1 | 9/2012 | Kamath et al. |
| 2012/0246106 A1* | 9/2012 | Atlas ............... A61B 5/14532 706/52 |
| 2012/0259191 A1 | 10/2012 | Shariati et al. |
| 2012/0259278 A1 | 10/2012 | Hayes et al. |
| 2012/0277723 A1 | 11/2012 | Skladnev et al. |
| 2012/0283694 A1* | 11/2012 | Yodfat ............... A61M 5/1723 604/504 |
| 2012/0289931 A1 | 11/2012 | Robinson et al. |
| 2013/0046281 A1 | 2/2013 | Javitt |
| 2013/0053818 A1 | 2/2013 | Estes et al. |
| 2013/0053819 A1 | 2/2013 | Estes |
| 2013/0053820 A1 | 2/2013 | Estes et al. |
| 2013/0102867 A1 | 4/2013 | Desborough et al. |
| 2013/0116649 A1 | 5/2013 | Breton et al. |
| 2013/0204186 A1 | 8/2013 | Moore et al. |
| 2013/0218126 A1 | 8/2013 | Hayter et al. |
| 2013/0237932 A1 | 9/2013 | Thueer et al. |
| 2013/0245563 A1 | 9/2013 | Mercer et al. |
| 2013/0253418 A1 | 9/2013 | Kamath et al. |
| 2013/0297334 A1 | 11/2013 | Galasso et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0025015 A1 | 1/2014 | Cross et al. |
| 2014/0031759 A1 | 1/2014 | Kouyoumjian et al. |
| 2014/0039383 A1 | 2/2014 | Dobbles et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066892 A1 | 3/2014 | Keenan et al. |
| 2014/0094766 A1 | 4/2014 | Estes et al. |
| 2014/0107607 A1 | 4/2014 | Estes |
| 2014/0114278 A1 | 4/2014 | Dobbles et al. |
| 2014/0121635 A1 | 5/2014 | Hayter |
| 2014/0128705 A1 | 5/2014 | Mazlish |
| 2014/0128803 A1 | 5/2014 | Dobbles et al. |
| 2014/0163517 A1 | 6/2014 | Finan et al. |
| 2014/0180240 A1 | 6/2014 | Finan et al. |
| 2014/0228627 A1 | 8/2014 | Soffer et al. |
| 2014/0228668 A1 | 8/2014 | Wakizaka et al. |
| 2014/0235981 A1 | 8/2014 | Hayter |
| 2014/0249500 A1 | 9/2014 | Estes |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0276583 A1 | 9/2014 | Chen et al. |
| 2014/0309615 A1 | 10/2014 | Mazlish |
| 2015/0018757 A1 | 1/2015 | Starkweather et al. |
| 2015/0025471 A1 | 1/2015 | Enggaard |
| 2015/0025495 A1 | 1/2015 | Peyser |
| 2015/0030641 A1 | 1/2015 | Anderson et al. |
| 2015/0045737 A1 | 2/2015 | Stefanski |
| 2015/0073337 A1 | 3/2015 | Saint et al. |
| 2015/0080789 A1 | 3/2015 | Estes et al. |
| 2015/0100038 A1 | 4/2015 | McCann et al. |
| 2015/0120323 A1 | 4/2015 | Galasso et al. |
| 2015/0148774 A1 | 5/2015 | Yao |
| 2015/0157794 A1 | 6/2015 | Roy et al. |
| 2015/0164414 A1 | 6/2015 | Matthews |
| 2015/0165119 A1 | 6/2015 | Palerm et al. |
| 2015/0217051 A1 | 8/2015 | Mastrototaro et al. |
| 2015/0217052 A1 | 8/2015 | Keenan et al. |
| 2015/0265767 A1 | 9/2015 | Vazquez et al. |
| 2015/0265768 A1 | 9/2015 | Vazquez et al. |
| 2015/0314062 A1 | 11/2015 | Blomquist et al. |
| 2015/0320933 A1 | 11/2015 | Estes |
| 2015/0328402 A1 | 11/2015 | Nogueira et al. |
| 2015/0351683 A1 | 12/2015 | Brauker et al. |
| 2015/0352282 A1 | 12/2015 | Mazlish |
| 2015/0352283 A1 | 12/2015 | Galasso |
| 2016/0000998 A1 | 1/2016 | Estes |
| 2016/0030669 A1 | 2/2016 | Harris et al. |
| 2016/0038673 A1 | 2/2016 | Morales |
| 2016/0082187 A1 | 3/2016 | Schiable et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |
| 2016/0213841 A1 | 7/2016 | Geismar et al. |
| 2016/0256629 A1 | 9/2016 | Grosman et al. |
| 2017/0182248 A1* | 6/2017 | Rosinko ............... A61M 5/1723 |

FOREIGN PATENT DOCUMENTS

| | | |
|---|---|---|
| DE | 20 2005 012 358 | 10/2005 |
| EP | 0 062 974 | 10/1982 |
| EP | 0 098 592 | 1/1984 |
| EP | 0 275 213 | 7/1988 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 1990/015928 | 12/1990 |
| WO | WO 1997/021457 | 6/1997 |
| WO | WO 1998/011927 | 3/1998 |
| WO | WO 1998/057683 | 12/1998 |
| WO | WO 1999/021596 | 5/1999 |
| WO | WO 1999/039118 | 8/1999 |
| WO | WO 1999/048546 | 9/1999 |
| WO | WO 2001/072360 | 10/2001 |
| WO | WO 2001/091822 | 12/2001 |
| WO | WO 2001/091833 | 12/2001 |
| WO | WO 2002/040083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |
| WO | WO 2008/073609 | 6/2008 |
| WO | WO 2009/032402 | 3/2009 |
| WO | WO 2009/035759 | 3/2009 |
| WO | WO 2010/045460 | 4/2010 |
| WO | WO 2010/097796 | 9/2010 |
| WO | WO 2014/062399 | 4/2014 |
| WO | WO 2014/074476 | 5/2014 |
| WO | WO 2014/134459 | 9/2014 |
| WO | WO 2014/172467 | 10/2014 |
| WO | WO 2015/191459 | 12/2015 |
| WO | WO 2016/004210 | 1/2016 |

OTHER PUBLICATIONS

"Using the Deltec Cozmo Insulin Pump Correction Bolus Feature" believed to be publicly available before May 5, 2008, pp. 36-41.

(56) References Cited

OTHER PUBLICATIONS

"Which Insulin Pump is Right for Me?", Albany Medical Center, Goodman Diabetes Service, Jan. 2006, 4 pages.
Asante Pearl, Insulin Pump User Manual, 2012, 180 pages.
Brown et al., "CGM, Pumps, and SMBG." American Diabetes Association—71$^{st}$ Scientific Sessions, San Diego, CA, Jun. 24-28, 2011, 38 pages.
Collins and Lee, "Microfluidic flow transducer based on the measurement of electrical admittance," *Lab Chip*, 2003, 12 pages.
Cox et al. "Prediction of Severe Hypoglycemia." *Diabetes Care*, vol. 30, No. 6, Jun. 2007, 4 pages.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
Medtronic News Release, "Medtronic Receives FDA Approval for World's First Insulin Pump with Real-time Continuous Glucose Monitoring," Apr. 13, 2006, 3 pages.
Patent Abstracts of Japan, vol. 1999, No. 04, and JP 11 010036, Apr. 30, 1999 and Jan. 19, 1999, Toray Ind. Inc.
*The Content of Investigational Device Exemption (IDE) and Premarket Approval (PMA) Application for Low Glucose Suspend (LGS) Device System*. Rockville, MD, Food and Drug Administration, 2011, 59 pages.
Walsh et al., "Guidelines for Insulin Dosing in Continuous Subcutaneous Insulin Infusion Using New Formulas from a Retrospective Study of Individuals with Optimal Glucose Levels", J. Diabetes Science and Technology, vol. 4 Issue 5, Sep. 2010 (8 pages).
Walsh et al., "Guidelines for Optimal Bolus Calculator Settings in Adults", J. Diabetes Science and Technology; vol. 5 Issue 1; Jan. 2011 (7 pages).

\* cited by examiner

OPERATING AN INFUSION PUMP SYSTEM

TECHNICAL FIELD

This document relates to an infusion pump system, such as a portable infusion pump system for dispensing insulin or another medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often need to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

In some circumstances, an infusion pump device can store (via input from a clinician or a user) a number of settings (e.g., dosage parameters or other settings) that are customized for the particular user. In one example, an infusion pump device can be programmed to store a user's insulin sensitivity (e.g., in units of mg/dL/insulin unit), which can be employed by the infusion pump system when calculating a correction bolus dosage for that particular user. In another example, an infusion pump device can be programmed to store a user's carbohydrate ratio (e.g., in units of g/insulin unit), which can be employed by the infusion pump system when calculating meal bolus dosage for that particular user. In many cases, these user-specific settings are manually input into the infusion pump device via user interface buttons on the infusion pump device. If any of these settings are erroneously input into the infusion pump system (e.g., due to a transcribing error or other error when manually inputting the data), the resulting consequences could lead to improper bolus dosage calculations, blood glucose levels that are unnecessarily too high or too low.

SUMMARY

Some embodiments an infusion pump system can be configured to control dispensation of medicine according to a closed-loop delivery mode and according to an open-loop delivery mode. In some circumstances, the infusion pump system can, during the closed-loop delivery mode, more accurately determines one or more user-specific settings, and then transition to the open-loop delivery mode in which one or more insulin dosages for dispensation are calculated and implemented based at least in part on the user-specific settings that were determined during the closed-loop delivery mode. As such, in particular embodiment, the infusion pump system can be programmed to enter a personal setting learning mode for purposes of identifying or updating customized values for the particular user's dosage parameters—even if the default or originally entered dosage parameters were inaccurate for the particular user. From there, the user can optionally exit the closed-loop delivery mode and instead operate the infusion pump system according to the open-loop delivery mode (which may use a basal delivery pattern and user-initiated bolus deliveries) that accesses and uses the customized values for purposes of providing accurate and user-specific bolus dosages, basal dosages, or both.

In one implementation, a method includes operating an infusion pump system to dispense insulin according to a closed-loop delivery mode; determining one or more user-specific dosage parameters based on feedback data received during the closed-loop delivery mode; storing the user-specific dosage parameters that were determined in one or more computer readable memory devices of the infusion pump system; transitioning to operate the infusion pump system to dispense insulin according to an open-loop delivery mode; and while the infusion pump system is operating in the open-loop delivery mode, calculating an insulin dosage to be dispensed based at least in part on the stored user-specific dosage parameters that were determined based on the feedback data received during the closed-loop delivery mode.

Such a method can, in some instances, optionally include one or more of the following features. Said transitioning can occur in response to detecting a transition trigger event. Said transition trigger event can include actuation of a user interface button indicating the user's acknowledgement to exit the closed-loop delivery mode. The method can further include receiving glucose information via wireless communication from a monitoring device, the glucose information being indicative of a blood glucose level of the user, wherein said feedback data received during the closed-loop delivery mode includes at least in part said glucose information. The infusion pump system can include a controller including a user interface display device, control circuitry arranged in a controller housing and being programmed to perform said determining, storing, and calculating operations. The infusion pump system can include a pump device having a pump housing that houses a drive system and an insulin reservoir, the controller housing being removably mountable to the pump housing so that the controller is electrically connected to the drive system. The user-specific dosage parameters that were determined based on the feedback data received during the closed-loop delivery mode can include values for a user's insulin sensitivity, carbohydrate ratio, insulin onset time, insulin on board duration, and basal rate profile.

In another implementation, a medical infusion pump system can include a portable pump housing that receives medicine for dispensation to a user, the pump housing at least partially containing a pump drive system to dispense the medicine through a flow path to the user; a controller that controls the pump drive system to dispense the medicine from the portable pump housing; and wherein the controller is configured to control the dispensation of medicine according to a closed-loop delivery mode in which the controller determines one or more user-specific settings and according to an open-loop delivery mode in which one or more insulin dosages for dispensation are based at least in part on the user-specific settings that were determined during the closed-loop delivery mode.

Such a system can, in some instances, optionally include one or more of the following features. The controller can be configured to transition from the closed-loop delivery mode to the open-loop delivery mode in response to detecting a transition trigger event. The transition trigger event can include actuation of a user interface button indicating the user's acknowledgement to exit the closed-loop delivery mode. Said one or more insulin dosages for dispensation during the open-loop delivery mode can include a suggested bolus dosage calculated and displayed by the controller during the open-loop delivery mode. The controller can determine the suggested bolus dosage during the open-loop delivery mode based at least in part on the user-specific setting of any of a user's insulin sensitivity and a user's carbohydrate ratio, said the user-specific setting being determined and stored by the controller during the closed-loop delivery mode. The controller can determine the suggested bolus dosage according to the function: Suggested Bolus Dosage=(Food Offsetting Component)+(Blood Glucose Correction Component)−(Insulin Load Correction Component), wherein each of the Food Offsetting Component, the Blood Glucose Correction Component, and the Insulin Load Correction Component can be dependent upon one of the user-specific settings that were determined during the closed-loop delivery mode. The controller can include a user interface including a display device and a plurality of user-actuatable buttons. The controller can include a controller housing that removably attaches to the pump housing. The controller can be electrically connected to the pump drive system when the controller housing is removably attached to the pump housing. The controller can be a reusable device and the pump housing and pump drive system are disposable and nonreusable. The user-specific settings that were determined during the closed-loop delivery mode can include values for a user's personal dosage parameters. The system can further include monitoring device that communicates glucose information to the controller, the glucose information being indicative of a blood glucose level of the user.

In another implementation, a portable insulin pump system includes a disposable and non-reusable pump device including: a pump housing that defines a space to receive an insulin cartridge; and a drive system to dispense insulin when the insulin cartridge is received by the pump housing, the drive system including a piston rod that is incrementally movable to apply a dispensing force; and a removable controller device including: a controller housing that is removably attachable to the pump housing to provide an electrical connection between the controller device and the pump device; control circuitry arranged in the controller housing to electrically communicate with the drive system in the pump housing; a user interface connected to the control circuitry, the user interface including a display and one or more user-selectable buttons; and a wireless communication device to receive glucose information from a wearable monitoring device, the glucose information being indicative of a blood glucose level of the user, wherein the removable controller device is configured to control the dispensation of medicine to a user according to a closed-loop delivery mode in which the controller determines customized dosage parameters that are specific to the user and according to an open-loop delivery mode in which insulin dosages for dispensation to the user are based at least in part on the customized dosage parameters that were determined during the closed-loop delivery mode.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings may indicate like elements.

DETAILED DESCRIPTION OF ILLUSTRATIVE EMBODIMENTS

Figure 1:
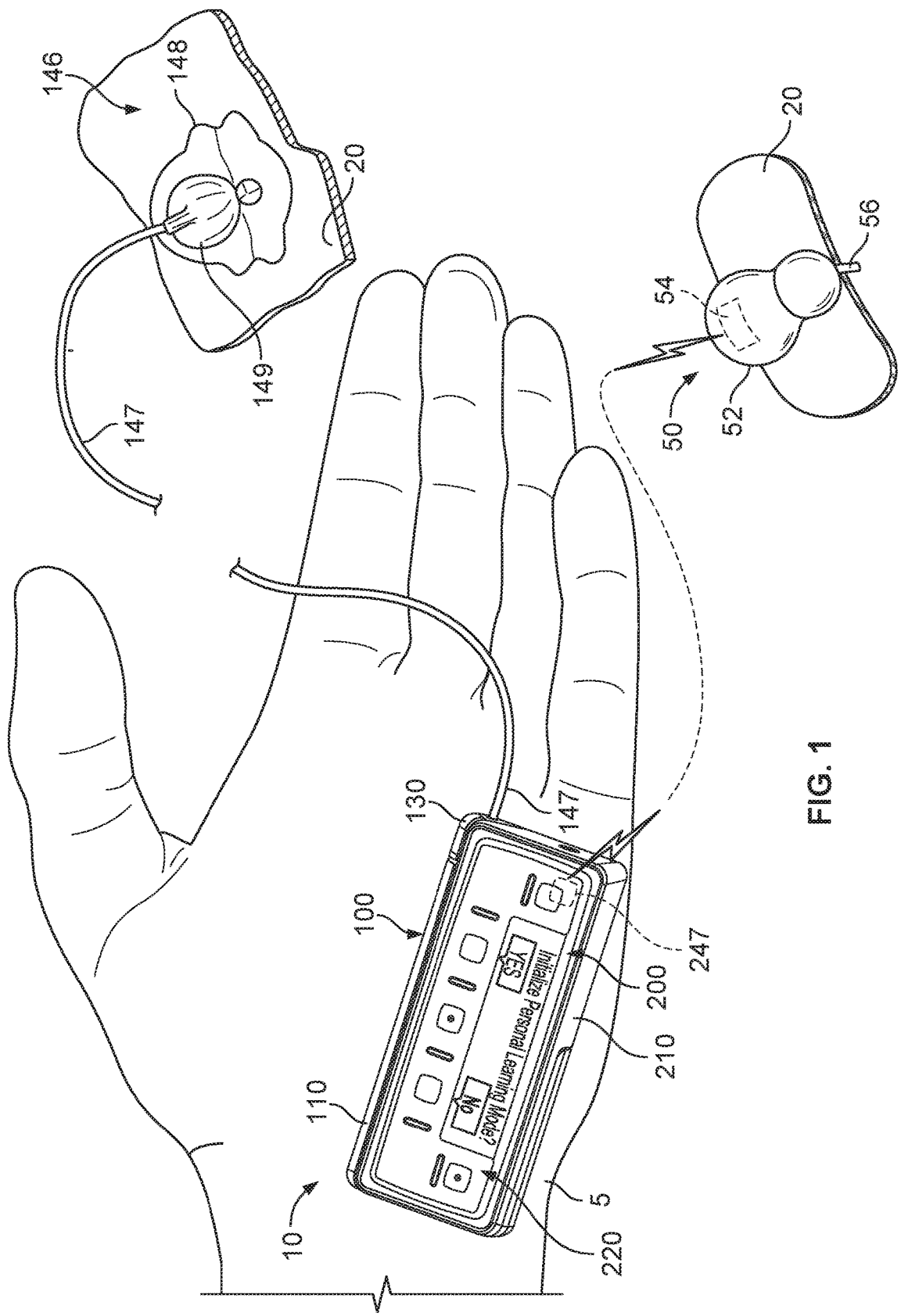
FIG. 1 is a perspective view of a first example infusion pump system, in accordance with some embodiments.

Referring to FIG. 1, some embodiments of an infusion pump system 1 can include a pump assembly 10 featuring a pump device 100 and a controller device 200. Optionally, the controller device 200 can be configured to releasably attach with the pump device 100. The controller device 200 can electrically communicate with the pump device 100 to control a drive system housed in the pump device 100 to dispense a medicine to a user (e.g., through a tube 147 of an infusion set 146 in this example). When the controller device 200 and the pump device 100 are assembled together, the user can (in some embodiments) conveniently wear the infusion pump system 1 on the user's skin under clothing, in a pouch clipped at the waist, or in the user's pocket while receiving the fluid dispensed from the pump device 100.

Briefly, in use, the pump device 100 in this embodiment is configured to removably attach to the controller device 200 in a manner that provides a secure fitting, an overall compact size, and a reliable electrical connection. For example, as described in more detail below in connection with FIG. 2, the controller device 200 can include a housing 210 having a number of features that mate with complementary features of the pump housing 110. In such circumstances, the controller device 200 can removably attach with the pump device 100 in a generally side-by-side configuration. The compact size permits the pump assembly 10 to be discrete and portable. The controller device 200 can receive user input for purposes of operating the infusion pump system 1. In some embodiments, as described further below in connection with FIGS. 4-7, the pump system 1 can be configured (e.g., appropriately designed and programmed) to operate in a personal settings learning mode in which the controller device 200 learns and stores one or more user-specific dosage parameters or other settings (e.g., the user's insulin sensitivity, the user's carb ratio, or other settings). For example, the controller device 200 can be configured to operate the infusion pump system 1 according to closed-loop delivery mode and an open-loop delivery mode. During operations under the closed-loop delivery mode, the controller device 200 is configured to determine and store one or more user-specific settings, such as a user's personal dosage parameters, which can be subsequently accessed during future closed-loop or open-loop operations (e.g., bolus dosage calculations and the like).

Still referring to FIG. 1, the infusion pump system 1 may optionally include a glucose monitoring device 50 in communication with the pump assembly 10 for the purpose of supplying data indicative of a user's blood glucose level to the controller device 200. In some embodiments, as described further below in connection with FIGS. 5A and 5B, the controller device 200 can utilize the data indicative of a user's blood glucose level during a closed-loop delivery mode to determine and/or update one or more user-specific dosage parameters. In some embodiments, as described further below in connection with FIG. 6, the controller device can also utilize the data indicative of a user's blood glucose level during an open-loop delivery mode, for example, to calculate a suggested bolus dosage based on the user-specific dosage parameters determined or updated during the closed-loop delivery mode.

The glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to a corresponding wireless communication device 247 housed in the pump system 10. In some embodiments, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some alternative embodiments, the monitoring device 50 can be in communication with the controller device 200 via a wired connection. In other embodiments of the infusion pump system 1, one or more test strips (e.g., blood test strips) containing a sample of the user's blood can be inserted into a strip reader portion of the pump system 1 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the controller device 200. In still other embodiments, characteristics of the user's blood glucose information can be entered directly into the pump system 10 via a user interface 220 on the controller device 200.

Figure 2:
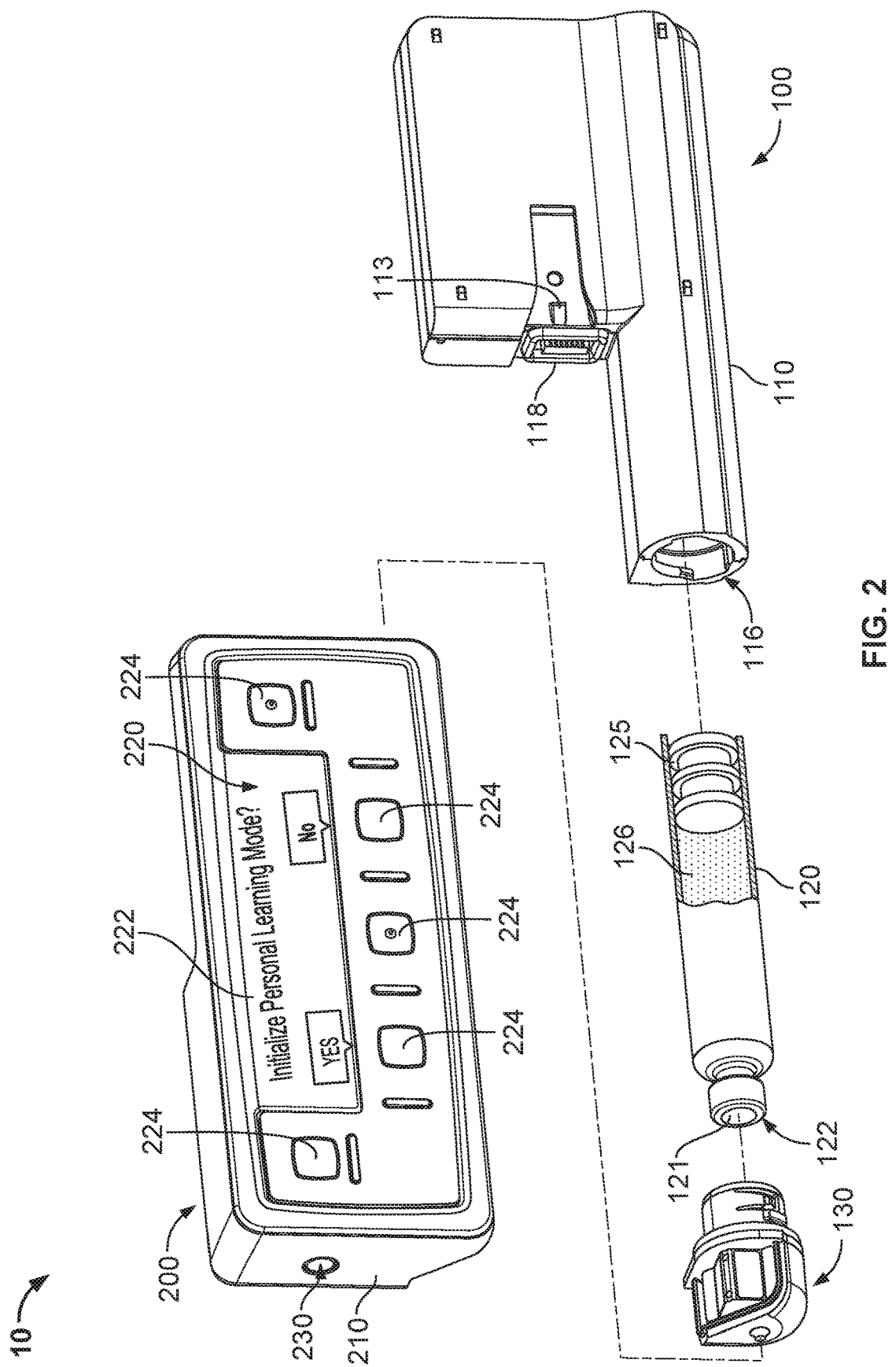
FIG. 2 is an exploded perspective view of an infusion pump assembly in accordance with some embodiments.

Referring now to FIG. 2, the pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (not shown) that advances a plunger 125 in the fluid cartridge 120 so as to dispense fluid therefrom. In this embodiment, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 10 can provide enhanced user safety as a new pump device (and drive system therein) is employed with each new fluid cartridge.

The pump assembly 10 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some embodiments, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 2, the controller device 200 can be removably attached to the pump device 100 so that the two components are mechanically mounted to one another in a fixed relationship. In some embodiments, such a mechanical mounting can also form an electrical connection between the removable controller device 200 and the pump device 100. For example, the controller device 200 can be in electrical communication with a portion of the drive system (show shown) of the pump device 100. In some embodiments, the pump device 100 can include a drive system that causes controlled dispensation of the medicine or other fluid from the cartridge 120. In some embodiments, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are mechanically attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Still referring to FIG. 2, the controller device 200 can include a user interface 220 that permits a user to monitor and actively control the operation of the pump device 100. In some embodiments, the user interface 220 can include a device 222 and one or more user-selectable buttons (e.g., several buttons 224 are shown in the embodiment of FIGS. 1-2). The display device 222 can include an active area in which numerals, text, symbols, images, or a combination thereof can be displayed. For example, the display device 222 can be used to communicate a number of settings or menu options for the infusion pump system 1 (FIG. 1). In this embodiment, the user may press one or more of the buttons to shuffle through a number of menus or program screens that show particular operational modes (e.g., closed-loop delivery mode and open-loop delivery mode), settings (e.g., user-specific dosage parameters) and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the modes and/or settings, or otherwise program the controller device 200 by pressing one or more buttons 224 of the user interface 220. For example, the user may press one or more of the buttons to change the operation of the infusion pump system 1 from a closed-loop delivery mode to an open-loop delivery mode. In some implementations, the display device 222 may also be used to communicate information regarding remaining battery life.

The pump assembly 10 can be configured to be portable and can be wearable and concealable. For example, a user can conveniently wear the pump assembly 10 on the user's skin (e.g., skin adhesive) underneath the user's clothing or carry the pump device 100 in the user's pocket (or other portable location) while receiving the medicine dispensed from the pump device 100. The pump assembly 10 depicted in FIG. 1 as being held in a user's hand 5 so as to illustrate its size in accordance with some embodiments.

This embodiment of the pump assembly 10 is compact so that the user can wear the portable pump assembly 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the pump assembly 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 2) of the fluid cartridge 120 and the tube 147 of the infusion set 146.

In some embodiments, the pump assembly 10 can be pocket-sized so that the pump device 100 and controller device 200 can be worn in the user's pocket or in another portion of the user's clothing. In some circumstances, the user may desire to wear the pump assembly 10 in a more discrete manner. Accordingly, the user can pass the tube 147 from the pocket, under the user's clothing, and to the infusion site where the adhesive patch can be positioned. As such, the pump assembly 10 can be used to deliver medicine to the tissues or vasculature of the user in a portable, concealable, and discrete manner.

In some embodiments, the pump assembly 10 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

In some embodiments, the pump assembly 10 can operate (during an open-loop mode, for example) to deliver insulin to the user by basal dosages, selected bolus dosages, or a combination thereof. A basal rate of insulin can be delivered in an incremental manner (e.g., dispense 0.25 U every fifteen minutes for a rate of 1.0 U per hour) to help maintain the user's blood glucose level within a targeted range during normal activity, when the user is not consuming food items. The user may select one or more bolus deliveries, for example, to offset the blood glucose effects caused by food intake, to correct for an undesirably high blood glucose level, to correct for a rapidly increasing blood glucose level, or the like. In some circumstances, the basal rate delivery pattern may remain at a substantially constant rate for a long period of time (e.g., a first basal dispensation rate for a period of hours in the morning, and a second basal dispensation rate for a period of hours in the afternoon and evening). In contrast, the bolus dosages can be more frequently dispensed based on calculations made by the controller device 200. For example, the controller device 200 can determine that the user's blood glucose level is rapidly increasing (e.g., by interpreting data received from the glucose monitoring device 50) and can administer appropriate bolus dosage of insulin to correct for the rapid increase in blood glucose level. In another example, the user can request (via the user interface 220) that the controller device 200 calculate and suggest a bolus dosage based, at least in part, on a proposed meal that the user plans to consume.

The basal and bolus insulin dispensed into the user's body may act over a period of time to control the user's blood glucose level. As such, the user can benefit from the embodiments of the infusion pump system 1 that can take into account different circumstances and information when determining a suggested amount of a basal or bolus dosage. For example, the controller device 200 may be triggered to calculate a suggested bolus dosage in response to the user's food intake. When calculating the bolus dosage, however, the user may benefit if the controller device 200 employed one or more user-specific dosage parameters that reflect the user's physiological response to insulin. In some embodiments, the controller device 200 can employ the user-specific dosage parameters in combination with data indicative of the user's blood glucose level, historical food intake data previously submitted by the user, the user's insulin load, and the like to provide an accurate dosage calculation. Exemplary information that can be derived from the user's blood glucose information that can be used by the controller device 200 in determining a bolus dosage can include the user's current blood glucose level, the rate of change in the user's blood glucose level, the $2^{nd}$ derivative of the user's blood glucose data, the shape and/or appearance of the user's blood glucose curve, or the like. In some embodiments, the controller device 200 can use information from previously entered meals and previously delivered insulin dosages when calculating a suggested bolus dosage. In these embodiments, information regarding previously entered meals and previously delivered insulin dosages from 12 hours or more (e.g., 24 hours, 12 hours, 8 hours, 6 hours, 0.5 hours, or the like) can be used in the bolus dosage calculations.

Figure 3:
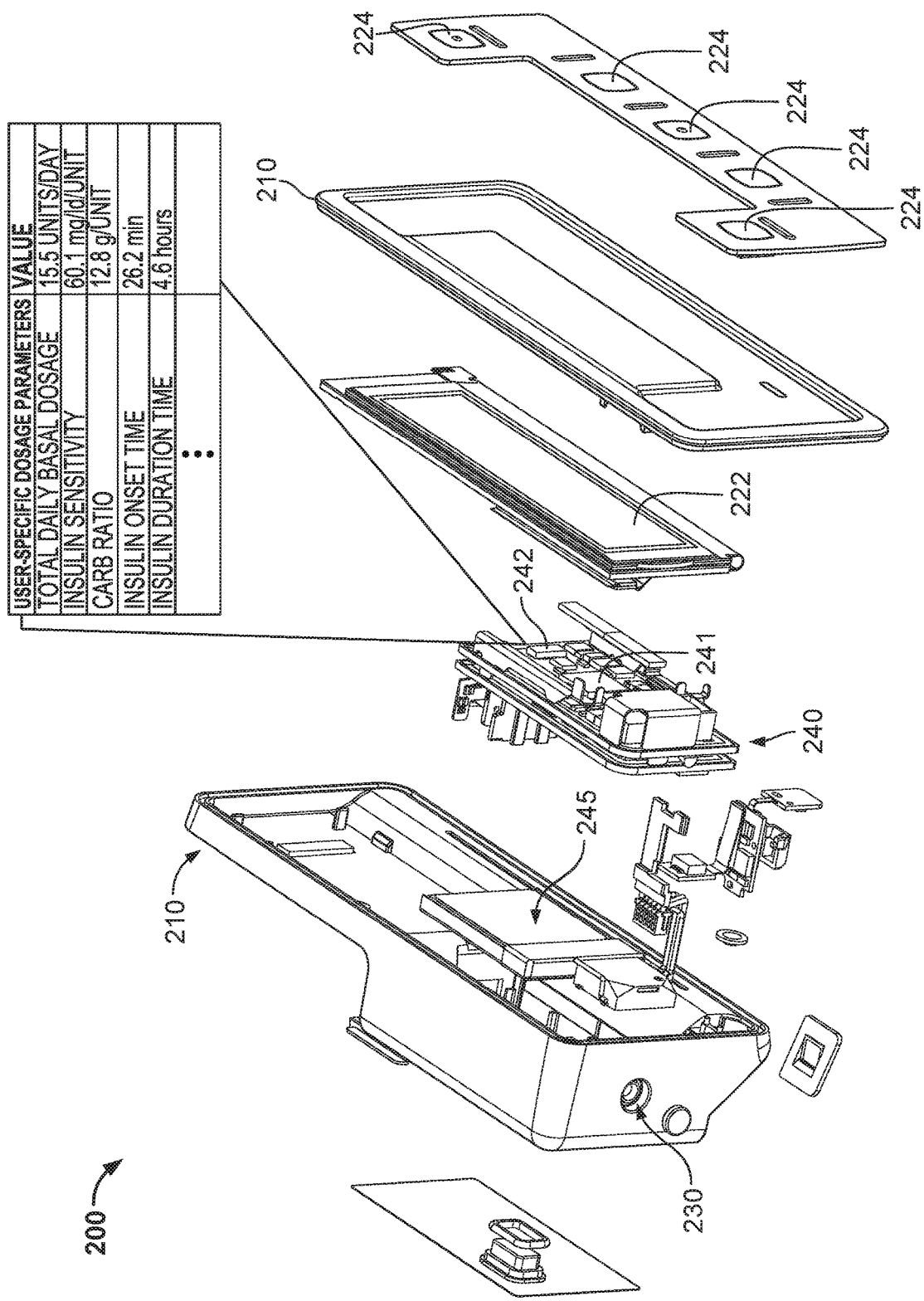
FIG. 3 is an exploded perspective view of a controller device for an infusion pump system, in accordance with some embodiments.

Referring now to FIG. 3, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific dosage parameters. One or more user-specific dosage parameters may be input by a user via the user interface 220. Further, as described further below in connection with FIGS. 5A and 5B, various user-specific dosage parameters can be automatically determined and/or updated by control operations implemented by the control circuitry 240 of the controller device 200. For example, the control circuitry 240 can determine and/or update one or more user-specific dosage parameters while the infusion pump system 1 operates in a closed-loop delivery mode. Whether determined automatically or received via the user interface 220, the control circuitry 240 can cause the memory device 242 to store the user-specific dosage parameters for future use during operations according to a closed-loop or open-loop delivery mode.

Such user-specific dosage parameters may include, but are not limited to, one or more of the following: insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour). Also, the control circuitry 240 can cause the memory device 242 to store any of the following parameters derived from the historical pump usage information: dosage logs, average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, and a frequency of cannula and tube primes per day. To the extent these aforementioned dosage parameters or historical parameters are not stored in the memory device 241, the control circuitry 240 can be configured to calculate any of these aforementioned dosage parameters or historical parameters from other data stored in the memory device 241 or otherwise input via the user interface 220.

The user interface 220 of the controller device 200 can include input components and/or output components that are electrically connected to the control circuitry 240. For example, the user interface 220 can include the display device 222 having an active area that outputs information to a user and buttons 224 that the user can use to provide input. Here, the display device 222 can be used to communicate a number of settings (e.g., user-specific dosage parameters) or menu options (e.g., options for switching between closed-loop and open-loop delivery modes) for the infusion pump system 1. In some embodiments, the control circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The control circuitry 240 can be programmable to cause the control circuitry 240 to change any one of a number of settings or modes of operation for the infusion pump system 1. In some embodiments, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

Figure 4:
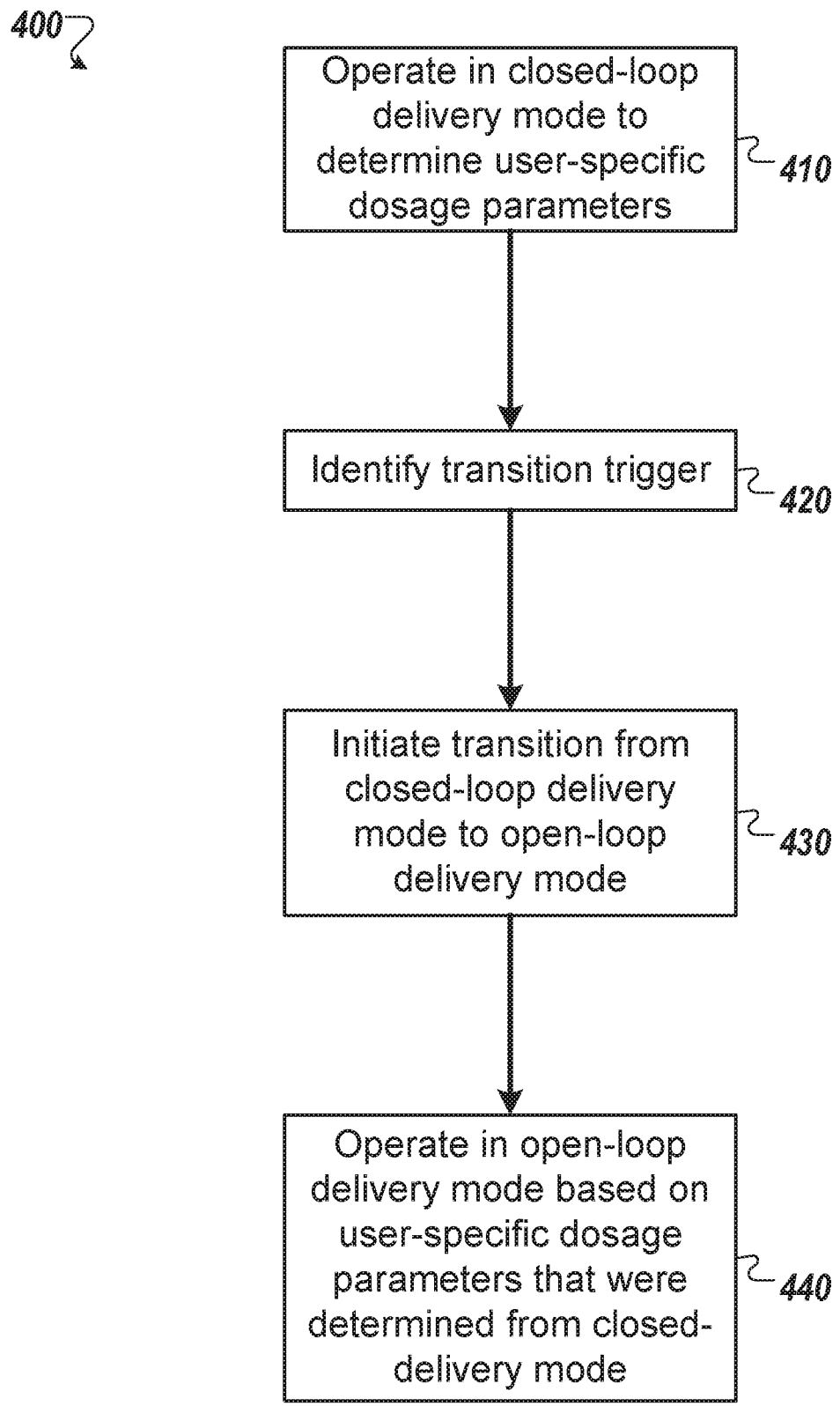
FIG. 4 is a flowchart of an example process for operating an infusion pump system according to multiple dosage delivery modes, in accordance with some embodiments.

Referring now to FIG. 4, the control circuitry of an infusion pump system can implement a process 400 of operating the infusion pump system according to multiple dosage delivery modes. Such a process 400, for example, can be implemented by the control circuitry 240 housed in the controller device 200 of an infusion pump assembly 10 (FIGS. 1-3). However, the description here not necessarily limited to any particular infusion pump system with respect to process 400, and the process 400 may be implemented using, for example, an infusion pump system in which the control circuitry and drive system components are housed together in a reusable pump unit. In another alternative example, the process 400 may be implemented using a remote device (a specially programmed smart phone device) that wireless communicates with an infusion pump system and is configured to calculate various user-specific dosage parameters during the closed-loop delivery mode.

Figure 5A:
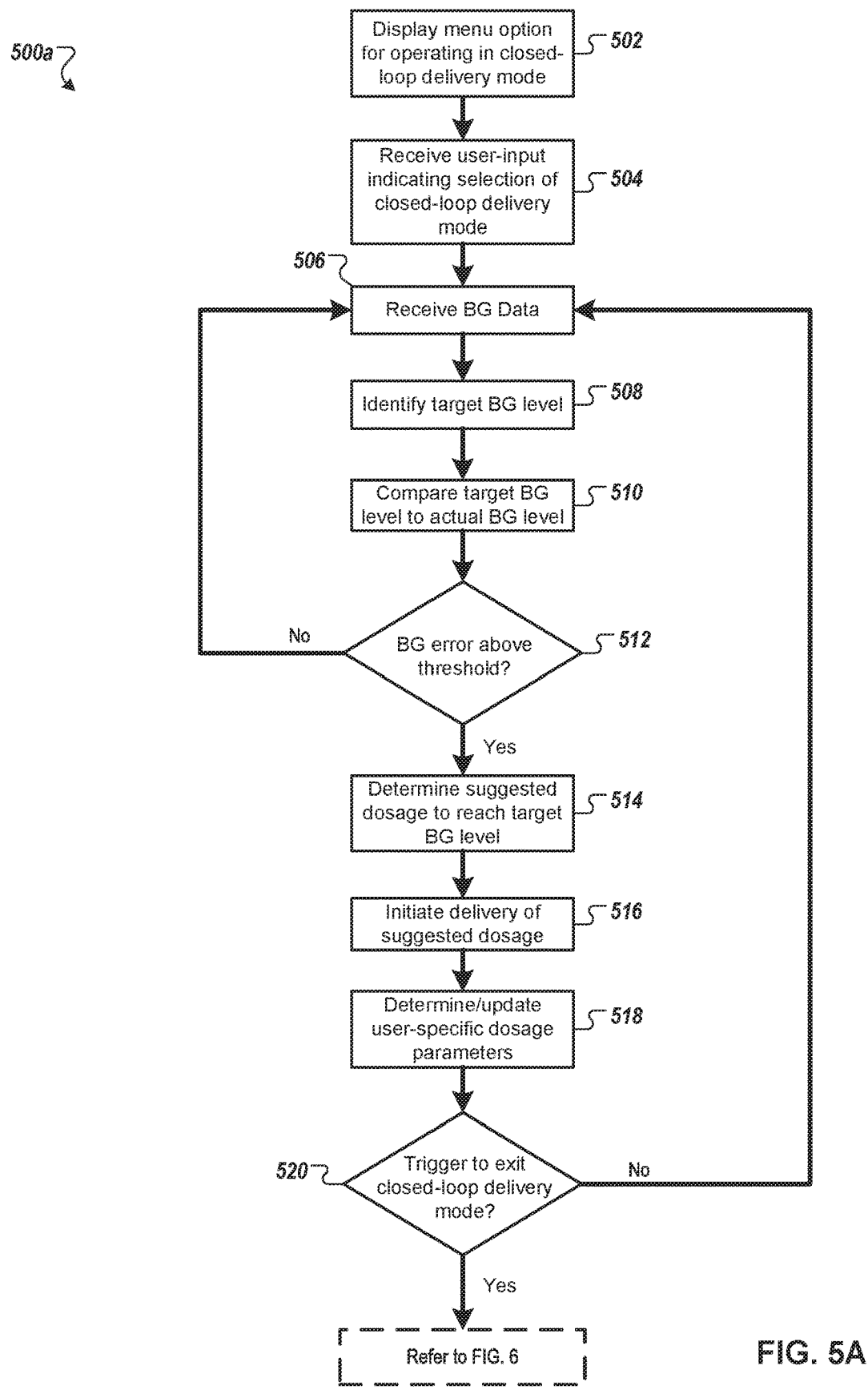
FIG. 5A is a flowchart of a first example process for operating an infusion pump system in a closed-loop delivery mode, in accordance with some embodiments.
Figure 5B:
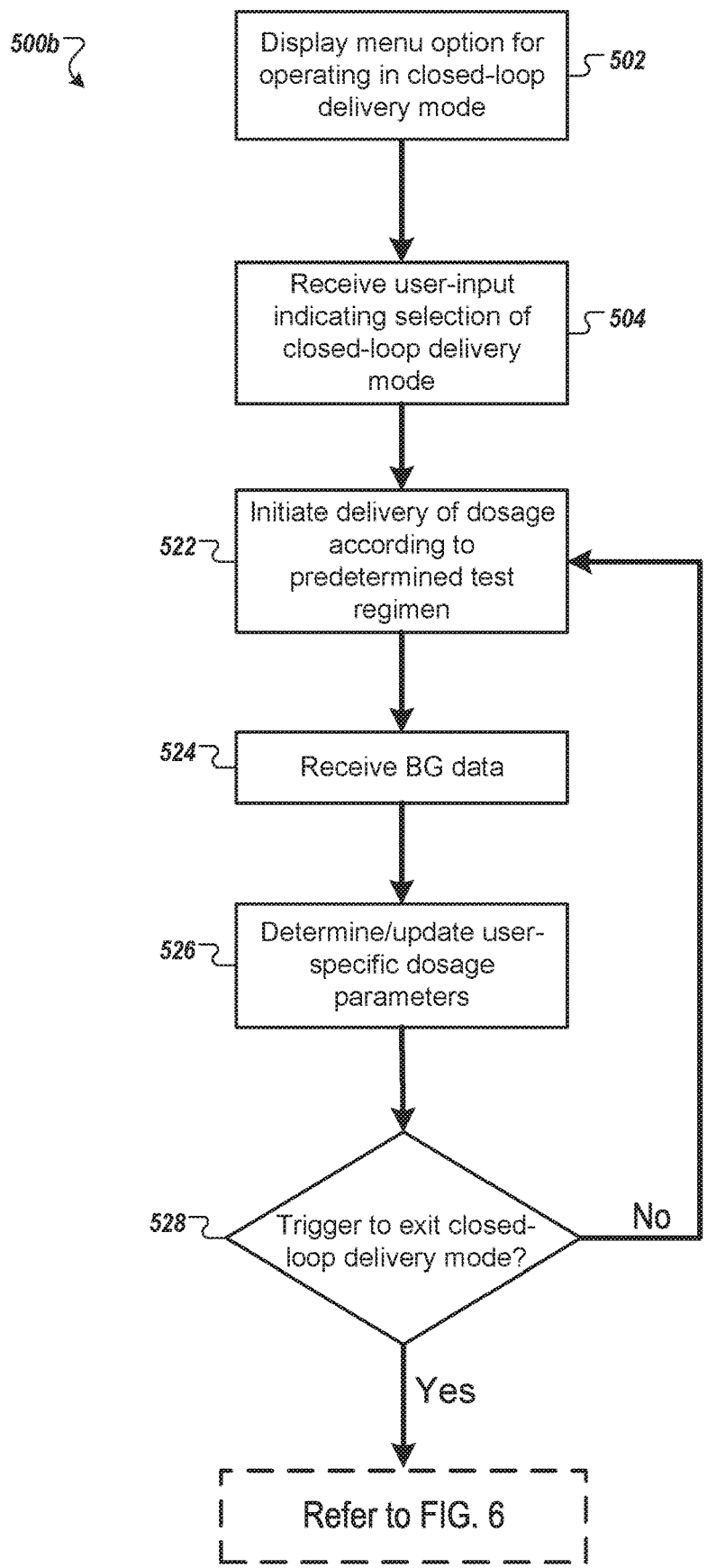
FIG. 5B is a flowchart of a second example process for operating an infusion pump system in a closed-loop delivery mode, in accordance with some embodiments.

In operation 410, the control circuitry operates the infusion pump system in a closed-loop delivery mode to determine one or more user-specific dosage parameters (see, e.g., FIGS. 5A and 5B). In the closed-loop delivery mode, the control circuitry can operate the medical device to autonomously (e.g., without user-interaction) alter the dispensation of medication to a user based upon a sensed physiological condition. For example, if the infusion pump system is dispensing insulin, closed-loop operations facilitated by the control circuitry may cause the infusion pump system to imitate a pancreatic beta cell (see FIG. 5A) so that the insulin dispensation is adjusted according to increases or decreases in the user's blood glucose level. This type of closed-loop control delivery mode can be executed by the control circuitry via any suitable control algorithm (e.g., a proportional-integral-derivative (PID), fuzzy logic, or model predictive control algorithm). Further, in some examples, the control circuitry can facilitate closed-loop operations that are consistent with a test regimen (see FIG. 5B). During such closed-loop operations, the control circuitry can monitor one or more sensor signals indicative of the user's response to the dispensation of medication. The sensory feedback signals can be used to implement a feedback control loop (see FIG. 5A) and/or to determine one or more user-specific dosage parameters. In one or more embodiments featuring an insulin-dispensing infusion pump system, suitable feedback signals may include, but are not limited to: physiological signals such as blood glucose data, activity data (e.g., heart rate, EKG heart activity, EMG muscle activity, respiration activity, etc.), blood pressure, and the like, glucagon delivery data, and food intake data. As noted above, in such embodiments, user-specific dosage parameters may include, but are not limited to: insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour).

In some embodiments, a user-specific dosage parameter can be determined as a function time and/or as a function of a monitored sensory feedback signal. As one non-limiting example, a series of multiple insulin sensitivities can be determined based on the time of day and/or based on the user's blood glucose level. The user-specific dosage parameters can be determined using any suitable mathematical technique. For example, in some embodiments, the control circuitry may employ a predefined data model (e.g., an empirical or statistical model expressed in an algebraic formula) and/or a regression analysis (e.g., a single or multi-variable regression analysis) to determine the parameters. The scope of the present disclosure is not limited to any particular process, algorithm, or technique for determining the various user-specific dosage parameters described herein.

Figure 6:
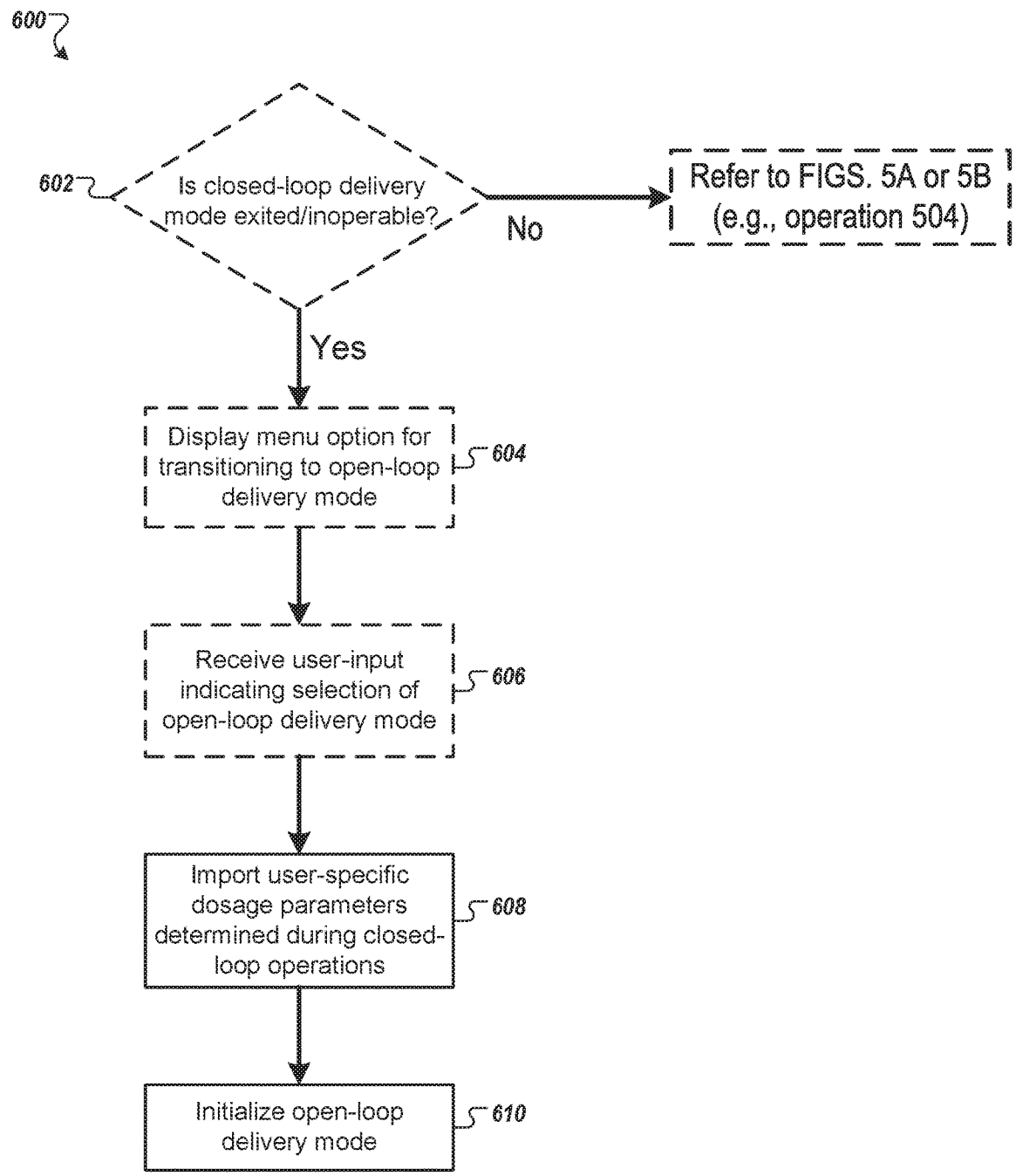
FIG. 6 is a flow chart of an example process for operating an infusion pump system to transition between a closed-loop delivery mode and an open-loop delivery mode, in accordance with some embodiments.

In operation 420, the control circuitry identifies a transition trigger signaling a change in the dosage delivery mode (see, e.g., FIG. 6). In one example, the user may access a menu option displayed by the infusion pump system and press a user interface button that triggers the user's requested change from the closed-loop delivery mode to an open-loop delivery mode. In another example, a transition trigger may arise upon expiration of a predetermined time period for operating in the closed-loop delivery mode.

In operation 430, the control circuitry initiates a transition from the closed-loop delivery mode to an open-loop delivery mode (see e.g., FIG. 6). For example, the infusion pump system may cease adjustments of the insulin delivery in response to changes in the user's glucose feedback data, and instead may prompt the user (via the user interface) to confirm that insulin delivery will return to a basal profile delivery according the open-loop delivery mode. In operation 440, the control circuitry operates the medical device in the open-loop delivery mode based on the user-specific dosage parameters determined during operations in the closed-loop delivery mode (see, e.g., FIG. 7). In the open-loop delivery mode, the control circuitry can operate the infusion pump system to dispense medication according to a selected basal delivery pattern and according to user-initiated bolus deliveries. For example, the user may manually input food intake data or blood glucose data and the control circuitry may calculate a suggested bolus dosage of insulin in response. As another example, the control circuitry may monitor a continuous glucose sensor on the user and provide an alert to the user when his/her blood glucose level suggests that a correction bolus dosage is needed. In some embodiments, the suggested bolus dosage is calculated based on the user-specific dosage parameters that were determined (and stored in the memory) during the closed-loop delivery mode.

FIG. 5A depicts a first example process 500a executable by the controller device 200 for operating the infusion pump system 1 in a closed-loop delivery mode to determine one or more user-specific dosage parameters. In operation 502, the controller device causes a menu option for operating in a closed-loop delivery mode to be displayed to the user via the display device 222 (see FIGS. 1 and 2). The user can accept or decline the option by selecting the appropriate user-interface buttons 224. In operation 504, the controller device 200 can receive user-input indicating selection of the closed-loop delivery mode. For example, the user can select the user interface button 224 corresponding to "YES" on the display screen presenting the menu option (see FIGS. 1 and 2).

In operation 506, the controller device 200 initiates an iterative sequence of operations that facilitate the closed-loop delivery of medication (e.g., insulin) by receiving blood glucose data. As described above, blood glucose data can be received from a glucose monitoring device 50 in wireless communication with the pump assembly 10 (or received from a blood glucose test strip reader). In operation 508, the controller device 200 identifies a target blood glucose level. For example, one or more target blood glucose levels may be stored in memory device 242 of the control circuitry 240. The target blood glucose levels may correspond to one or more monitored sensory feedback signals. For instance, the target blood glucose level may vary according to the user's food intake and/or physiological status. As one example, the member device 242 stores data indicating at least a fasting target blood glucose level and a postprandial target blood glucose level. In some embodiments, a target blood glucose level can be expressed as a range. In some embodiments, the target blood glucose levels can be manually submitted to the controller device 200 via the user interface 220. In some embodiments, the target blood glucose levels can be determined statistically or empirically by the controller device 200 as a user-specific dosage parameter based on previous iterations of a closed-loop delivery scheme. In operation 510, the controller device 200 compares the user's actual blood glucose level (as indicated by the received blood glucose data) to the identified target blood glucose level to ascertain a blood glucose error. In operation 512, the controller device determines whether the blood glucose error is above a predetermined threshold. In operation 514, if the controller device 200 concludes that the actual blood glucose error is above a predetermined threshold (512), a correction dosage to correct the blood glucose error is determined. Otherwise (512), the controller device 200 returns to operation 506 to await the receipt of further blood glucose data. In some embodiments, the correction dosage is determined via suitable PID control calculations, fuzzy logic control calculations, and/or model predictive control calculations. In operation 516, the controller device 200 initiates delivery of the correction dosage. For example, as described above, the controller device 200 can issue one or more electronic control signals to the drive system of the pump device 100 to cause the dispensation of the correction bolus.

In operation 518, the controller device 200 determines (including determining a new value or updating a previously stored value) one or more user-specific dosage parameters (e.g., insulin sensitivity, carbohydrate ratio, insulin onset time, insulin on board duration, and basal rate profile). For example, the controller device 200 may initially calculate the dosage parameters after one or more iterations of the closed-loop delivery scheme and continue to update the dosage parameters during future iterations. Alternatively, one or more default dosage parameters may be manually input via the user interface 220, and subsequently updated during the closed-loop delivery mode. In some embodiments, the user-specific dosage parameters can be determined or updated based on historical sensory feedback data (e.g., historical blood glucose data) and historical pump-usage data generated during the closed-loop delivery operations. As noted above, the user-specific dosage parameters can be determined using any suitable mathematical technique (e.g., a predefined data model and/or a regression analysis). As one example, a regression analysis approximating the relationship between the correction dosage (refer to operation 516, described above) and blood glucose level can be used to determine an insulin sensitivity parameter that is specific to the user (because various users will respond differently to correction dosages of insulin).

In operation 520, the controller device 200 can detect a trigger to exit the closed-loop delivery mode. In one example, the user may access a menu option displayed by the controller 200 and press a user interface button 224 that triggers the user's requested change from the closed-loop delivery mode to an open-loop delivery mode. In another example, a transition trigger may arise upon expiration of a predetermined time period for operating in the closed-loop delivery mode. If the controller device 200 detects a trigger to exit the closed-loop delivery mode (520), it initiates a transition sequence (see FIG. 6). Otherwise (520), the controller device 200 returns to operation 506 to await the receipt of further blood glucose data (and operations under the closed-loop delivery mode).

FIG. 5B depicts a second example process 500b executable by the controller device 200 for operating the infusion pump system 1 in a closed-loop delivery mode to determine one or more user-specific dosage parameters. Similar to the example process 500a of FIG. 5A, in operation 502, a menu option for operating in a closed-loop delivery mode is displayed to the user via the display device 222 (see FIGS. 1 and 2). The user can accept or decline the option by selecting the appropriate user-interface buttons 224. In operation 504, the controller device 200 receives user-input indicating selection of the closed-loop delivery mode (e.g., the user can select the user interface button 224 corresponding to the "YES" option on the display device 222).

In operation 522, the controller device 200 initiates the delivery of at least one medicine dosage (e.g., a predetermined, test bolus of insulin) according to a test regimen. In some embodiments, the test regimen is designed to produce data that can be used to update or determine one or more user-specific dosage parameters. Accordingly, a suitable test regimen may include a plurality of medicine dosages delivered across a predefined time period. In some embodiments, the test regimen may include a schedule of two or more dosages delivered at predetermined times. For example, a suitable test regimen may provide for X number of medicine dosages (where X is any non-negative whole number) to be delivered at two-hour intervals across a specified time period (e.g., during a time of day that the user is expected to be sleeping or otherwise fasting). In some embodiments, the test regimen may include a dynamic schedule of two or more dosages. In such embodiments, the dosage amount and delivery time may vary according to the user's measured bodily response to the medicine. For example, a suitable test regimen may provide for X number of medicine dosages to be delivered across a specified time period when the user's blood glucose level is determined to be at or above a predetermined threshold. Of course, the present disclosure is not limited to these particular example techniques. Any appropriate test regimen involving a planned dispensation of medicine is within the scope of this disclosure.

In operation 524, the controller device 200 receives blood glucose data. As described above, blood glucose data can be received from a glucose monitoring device 50 in wireless communication with the pump assembly 10 (or received from a blood glucose test strip reader). The blood glucose data received in operation 524 as well as other sensory feedback signals and pump usage data can be stored in a memory device 242 included in the control circuitry 240 of the controller 200. In operation 526, the controller device 200 determines or updates one or more user-specific dosage parameters (e.g., insulin sensitivity, carbohydrate ratio, insulin onset time, insulin on board duration, and basal rate profile). For example, the controller device 200 may initially calculate the dosage parameters after one or more iterations of the closed-loop delivery scheme and continue to update the dosage parameters during future iterations. Alternatively, one or more default dosage parameters may be manually input via the user interface 220, and subsequently updated during the closed-loop delivery mode. In this embodiment, the controller device 200 can determine or update the user-specific dosage parameters based on historical data (e.g., historical pump data and/or historical sensory feedback data) generated during the test regimen initiated in operation 522. As noted above, the user-specific dosage parameters can be determined using any suitable mathematical technique (e.g., a predefined data model and/or a regression analysis).

In operation 528, the controller device 200 can detect a trigger to exit the closed-loop delivery mode. For example, as previously described, the transition trigger may arise upon expiration of the predefined time period for operating in the closed-loop delivery mode. In another example, the transition trigger may arise upon the control circuitry confirming that all dosages of the test regimen (refer to operation 522) have been delivered and the blood glucose data responsive to the test regimen is received. If the controller device 200 detects a trigger to exit the closed-loop delivery mode (528), it initiates a transition sequence (see FIG. 6). Otherwise (528), the controller device 200 returns to operation 522 to continue the test regimen.

FIG. 6 depicts an example process 600 executable by the controller device 200 for operating an infusion pump system to transition between a closed-loop delivery mode and an open-loop delivery mode. In operation 602, the controller device 200 can determine if the closed-loop delivery mode has been exited (e.g., upon detection of a transition trigger, for example, as described above) or is otherwise inoperable. As one example, the controller device 200 may determine that a closed-loop delivery mode is completed by confirming that all dosages of a test regimen (see operation 522 of FIG. 5B) have been delivered and the blood glucose data responsive to the test regimen is received. As another example, the controller device 200 may determine that a closed-loop delivery mode is completed by receiving a trigger signal caused by the user engaging the user interface 220. For instance, the user may interact with the user interface buttons 224 to select on option to terminate the closed-loop delivery mode. As yet another example, the controller device 200 may determine that the closed-loop delivery mode is inoperable by detecting the disconnecting or malfunctioning of one or more feedback sensors (e.g., the blood glucose monitoring device 50). If the controller device 200 determines that the closed-loop delivery mode is complete or otherwise inoperable (602), it displays (e.g., via the display device 222 shown in FIGS. 1 and 2) a menu option for transitioning to an open-loop delivery mode in operation 604.

In any event, the user can accept or decline the option by selecting the appropriate user-interface buttons 224. In operation 606, the controller device 200 receives user-input indicating selection of the open-loop delivery mode. For example, the user can select the user interface button 224 corresponding to "YES" on the display screen presenting the menu option (see FIGS. 1 and 2). In response to the user's acceptance of the menu option, the controller device 200 imports (e.g., stores for access during the open-loop delivery mode) the user specific dosage parameters that were determined during closed-loop operations in operation 608, and initializes the open loop delivery mode in operation 610.

Figure 7:
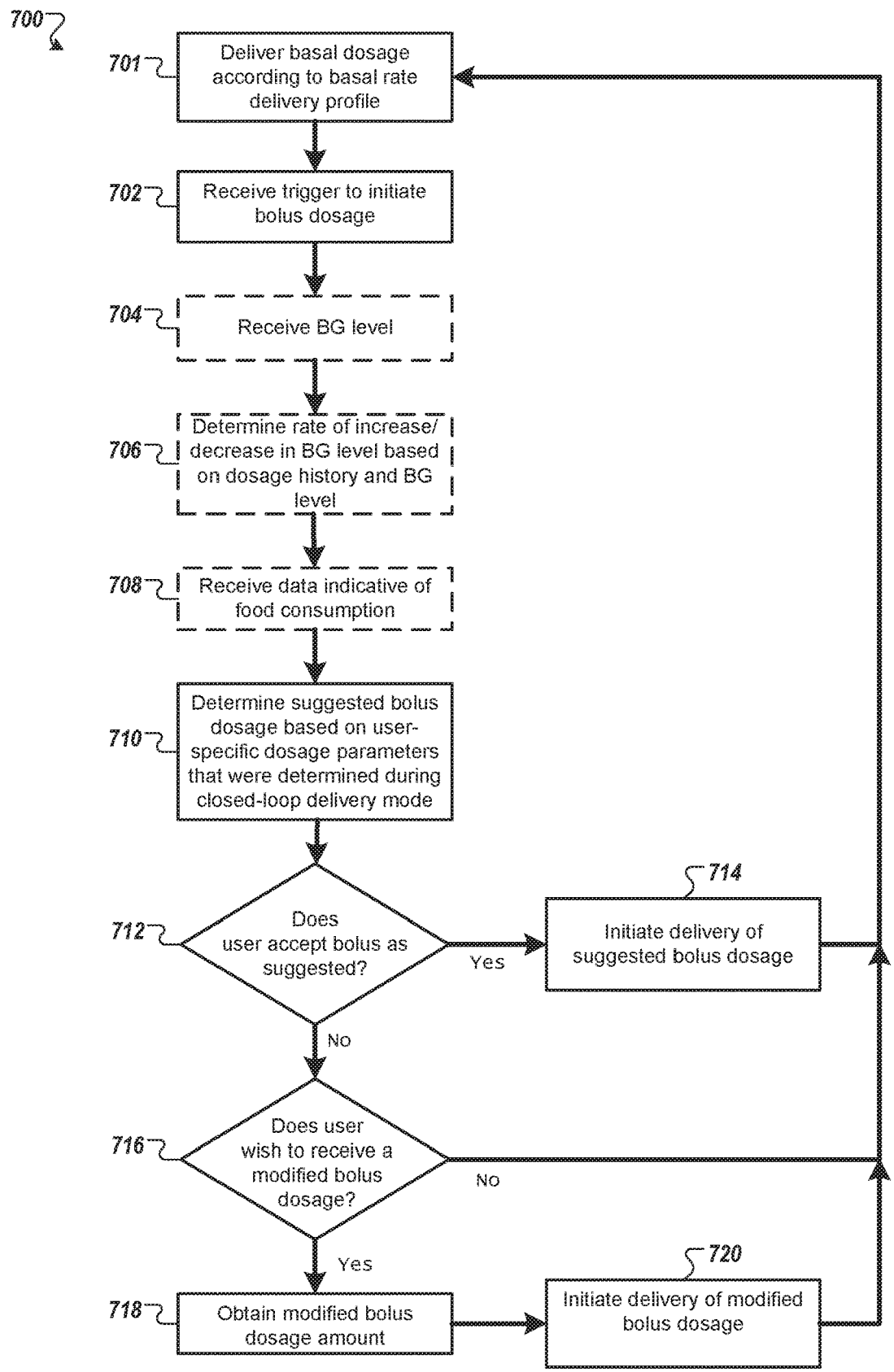
FIG. 7 is a flow chart of an example process for operating an infusion pump system in an open-loop delivery mode, in accordance with some embodiments.

FIG. 7 depicts a process 700 for operating an infusion pump system in an open-loop delivery mode, where medicine dosages (e.g., bolus dosages of insulin) are calculated in response to a request by the user and/or suggested by the controller device and confirmed by the user. In some embodiments, the controller device 200 may implement one or more operations of the process 700 to determine and suggest an insulin bolus dosage which includes a food offsetting component, a blood glucose correction component, and an insulin load correction component. The food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. This component can be derived from one or more user-specific dosage parameters (e.g., insulin sensitivity and carbohydrate ratio), data indicative of a user's blood glucose level (e.g., the user's current blood glucose level) and the recent rate of change in the user's blood glucose level. The insulin load correction component can also take into account one or more user-specific dosage parameters (e.g., insulin onset time and insulin on board duration), as well as historical data indicative of insulin that has been previously received and food that has been previously consumed, but has not acted on the user. For example, the delay between a subcutaneous delivery of a bolus dosage of insulin and the peak plasma insulin level achieved from this bolus can be one hour or more. Additionally, the bolus dosage may not enter the subcutaneous tissue all at once. As such, the effect of the bolus can peak at about one to two hours and then decay in a predictable manner over as much as eight hours or. Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the insulin load information can be determined by the controller device 200 on a periodic basis so that the user can be aware of the previously dispensed insulin which has not yet acted in the user's body. In a similar manner, food that has been previously consumed does not instantaneously act on the user and have its effects quickly decay. Depending on the type of food consumed, the effects of the food can be delayed and then slowly decay over time. In particular embodiments, the insulin load correction component may correct for the delayed effects of both previously delivered insulin and previously consumed food items.

Referring in more detail to FIG. 7, in operation 701, the controller device can cause the pump system to dispense basal dosages according to a basal rate delivery profile. The basal rate delivery profile can be stored in the memory of the controller device, and can optionally be updated based upon the dosage parameters that were determined during the closed-loop delivery mode. In this embodiment, the basal dosages are dispensed in an incremental manner (e.g., dispense 0.25 U every fifteen minutes for a rate of 1.0 U per hour during the period of 8:00 AM to 9:00 PM, and dispense 0.15 U every fifteen minutes for a rate of 0.6 U per hour during the period between 9:00 PM to 8:00 AM) to help maintain the user's blood glucose level within a targeted range during normal activity act selected periods of the day.

In operation 702, the controller device 200 can receive a trigger to initiate a bolus dosage calculation. Exemplary triggers that can cause the controller device 200 to initiate a bolus dosage calculation can include a user input of food intake data (e.g., via the user interface 220), a user request for a bolus dosage, the user's blood glucose level exceeding a predetermined threshold level, the user's blood glucose level increasing at a high rate greater than a predetermined threshold rate, or the like. In some embodiments, the suggested bolus dosage value can be calculated based on at least two of the three components as previously described: the food offsetting component, the blood glucose correction component, and the insulin load correction component. It should be understood from the description herein that the components can be contemporaneously calculated to provide the suggested bolus dosage value or, alternatively, calculated in discrete steps and then combined to provide the suggested bolus dosage value.

In operation 704, the controller device 200 receives the user's current blood glucose level. As described above, the user's current blood glucose level can be received via wireless communication from the glucose monitoring device 50 (or received from a blood glucose test strip reader, or entered manually by the user via the user interface 220). In operation 706, the controller device 200 can determine a rate of change (e.g., increase or decrease) based on the dosage history and the blood glucose level. Alternatively, the user may manually enter the rate-of-change information for his or her blood glucose level (rather than this information being determined by the controller device 200). For example, when using a blood glucose test strip reader, the test strip reader may store blood glucose measurements performed by the user, which can be used to determine the rate of change in the user's blood glucose level. When prompted by the controller device 200, the user may enter the most recent rate of change data. In operation 708, the user can optionally enter data indicative of food intake (e.g., a meal that is about to be consumed, a meal that has recently been consumed, or the like). For example, if the user is testing his or her blood glucose level before consuming a meal, the user may input such food intake information when inputting the blood glucose level.

After the user's blood glucose information is obtained (e.g., via operations 704-708), in operation 710, the controller device 200 can determined a suggested bolus dosage based on the obtained data and the user-specific dosage parameters that were determined during the closed-loop delivery mode. As noted above, in some embodiments, the suggested bolus dosage value can be calculated by the controller device 200 based on at least one, but preferably two or more of the three following components: the food offsetting component (which employs the value for the user's carb ratio that was, in this embodiment, calculated during the closed-loop delivery mode), the blood glucose correction component (which employs the value for the user's insulin sensitivity that was, in this embodiment, calculated during the closed-loop delivery mode), and the insulin load correction component. In such embodiments, the food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. The insulin load correction component can take into account insulin that has been previously received and food that has been previously consumed, but has not acted on the user. One non-limiting example is described below:

Suggested Bolus Dosage=(Food Offsetting Component)+(Blood Glucose Correction Component)−(Insulin Load Correction Component), where Food Offsetting Component=(Carbohydrate Intake)*(Insulin to Carb. Ratio), where Carbohydrate Intake represents the number of grams of carbohydrates consumed (or to be consumed) and Insulin to Carb. Ratio represents a user-specific ratio (which was preferably determined and stored during the closed-loop mode during this embodiment) of the amount of insulin required to offset the consumption of a gram of carbohydrates (e.g., 14.8 U/g or the like).

Blood Glucose Correction Component=(Current Blood Glucose Level−Target Glucose Level)*Insulin Sensitivity, where Current Blood Glucose Level represents the most recent blood glucose level, Target Glucose Level represents the user's desired blood glucose level, Insulin Sensitivity represents a user-specific value (which was preferably determined and stored during the closed-loop mode during this embodiment) that correlates the number of units of insulin required to alter the user's blood glucose level by 1 mg/dL.

Insulin Load Correction Component=Insulin Load−(Carb. Load)*Insulin to Carb Ratio, where Insulin Load represents the units of previously delivered insulin that have not yet acted on the user, Carb. Load represents the grams of carbohydrates that have been consumed, but have not acted on the user's blood glucose level, and Insulin to Carb. Ratio represents a user-specific ratio (which was preferably determined and stored during the closed-loop mode during this embodiment) of the amount of insulin required to offset the consumption of a gram of carbohydrates.

In operation 712, the controller device 200 can determine if the user accepts the suggested bolus dosage. For example, the user can select the user interface button 224 corresponding to the "YES" or "NO" option presented on the display device 222 to accept or decline the suggested bolus dosage. In operation 714, if the accepts the suggested bolus dosage (712), the controller device 200 can initiate delivery of the suggested bolus dosage by the pump device 100. If the user declines the suggested bolus dosage (712), the controller device 200 can prompt the user for a modified dosage. In operation 716, the controller device 200 can determine if the user wishes to receive a modified bolus dosage. In operation 718, if the user wishes to receive a modified bolus dosage (716), the controller device 200 can obtain the modified bolus dosage. For example, the user can enter a modified bolus dosage or provide additional data that can be used to calculate a modified dosage via the user interface 220. In operation 720, the controller device 200 can initiate delivery of the modified bolus dosage by the pump device 100. After a suggested (714) or modified (720) bolus dosage has been initiated, or after the user has declined the suggested (712) and modified dosages (716), the process 700 can return to operation 702, where the controller device 200 can wait for a subsequent trigger to initiate a bolus dosage calculation.

Figure 8:
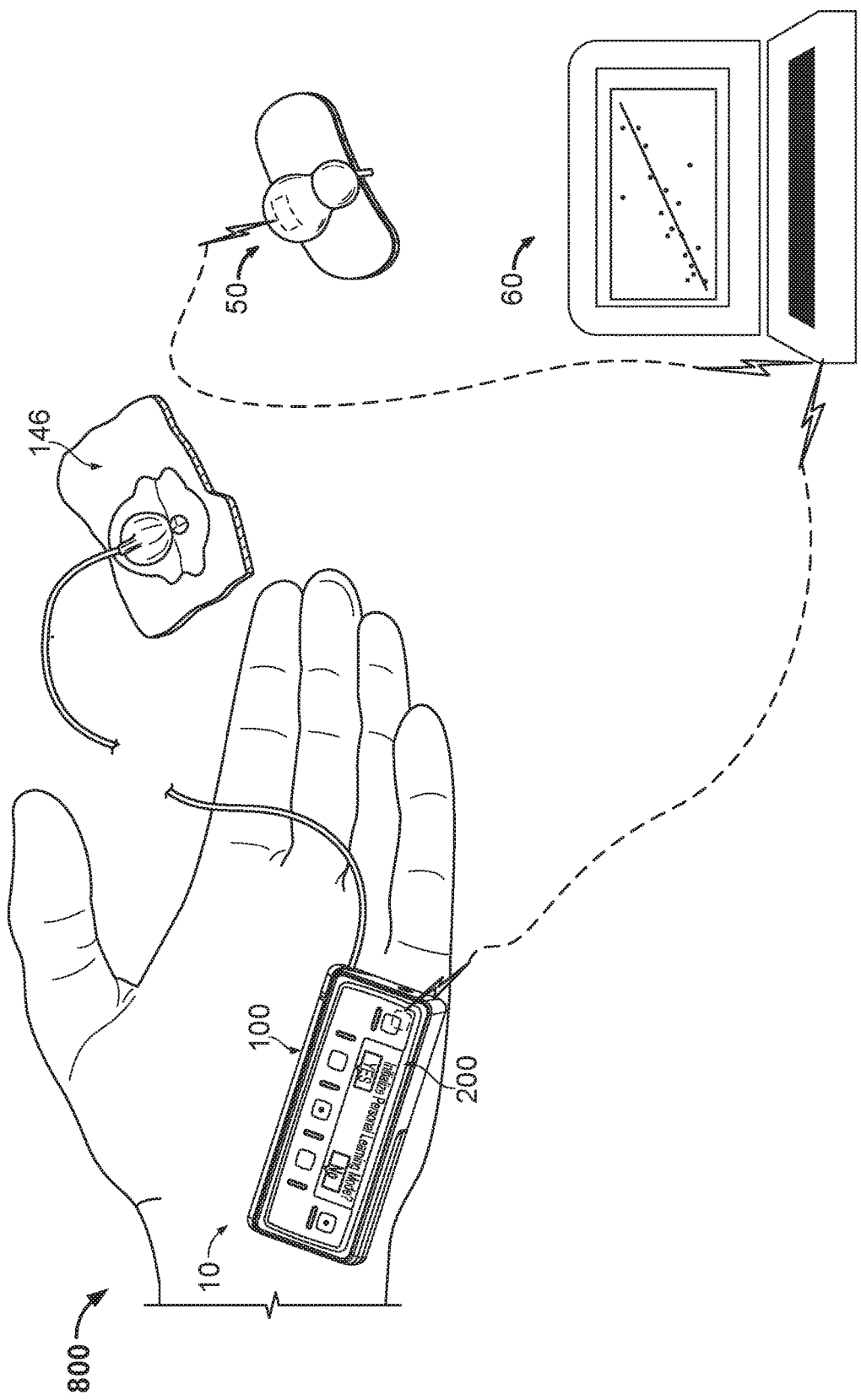
FIG. 8 is a perspective view of a second example infusion pump system, in accordance with some embodiments.

Referring now to FIG. 8, some embodiments of an infusion pump system 800 can include a pump assembly 10, featuring a controller device 200 and a pump device 100, mating with an infusion set 146 and a glucose monitoring device 50 (similar to previous embodiments described above with reference to FIGS. 1 and 2). The infusion pump system 800 further includes a computing device 60 in wireless communication with the controller device 200 of the pump assembly 10. In general, the term "computing device" refers to any appropriate type of data processing device capable of running operating systems and application programs. Example computing devices can include a general-purpose personal computer (PC), Macintosh, workstation, UNIX-based workstation, a blade server, a handheld computer, a tablet computing device, a personal digital assistant (PDA), a smartphone, or any appropriate combination of any two or more of these data processing devices or other data processing devices. The computing device 60 can provide additional processing power to the infusion pump system 800 for executing complex mathematical calculations and algorithms. Thus, the computing device 60 can be configured (e.g., appropriately designed and programmed) to execute a suitable program application for determining and/or updating one or more user-specific dosage parameters. As one example, the computing device 60 may determine and/or update one or more user-specific dosage parameters based on blood glucose data received from the glucose monitoring device 50 and pump-usage data received from the controller device 200. The computing device 60 can transmit the user-specific parameters back to the controller device 200 for use in future open-loop and/or closed-loop operations.

Figure 9:
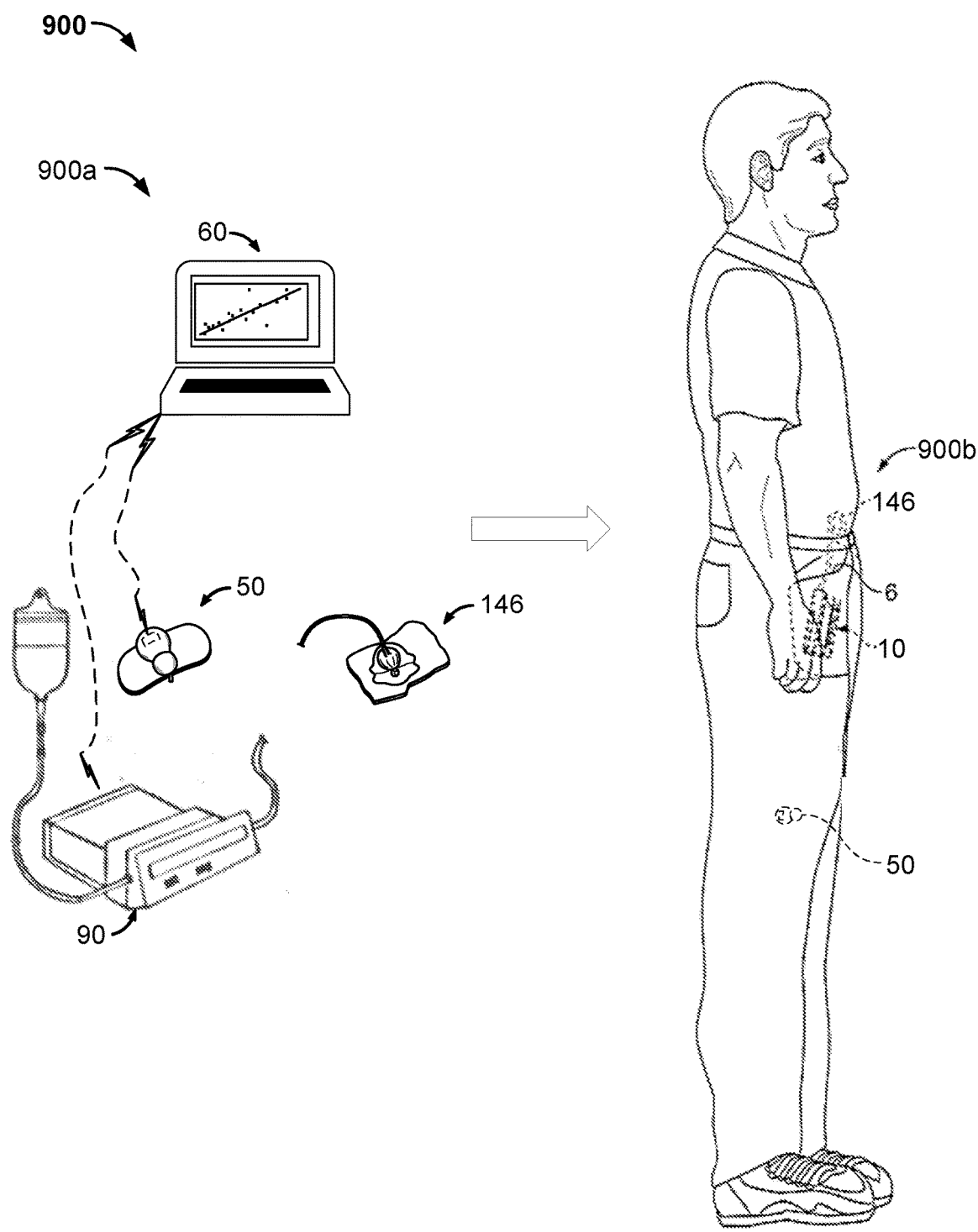
FIG. 9 is a perspective view of a third example infusion pump system, in accordance with some embodiments.

Referring now to FIG. 9, an infusion pump system 900 can include a bedside infusion pump subsystem 900a and a portable infusion pump subsystem 900b. The bedside infusion pump subsystem 900a includes a bedside infusion pump assembly 90 mating with an infusion set 146, a glucose monitoring device 50, and a computing device 60. Similar to the previous embodiments described above with respect to FIG. 8, the computing device 60 can receive data from the bedside infusion pump assembly 90 and the glucose monitoring device 50 for the purpose of determining one or more user-specific parameters. The portable infusion pump subsystem 900b features a portable pump assembly 10 (see FIGS. 1 and 2) that is pocket-sized so that the pump device 100 and controller device 200 can be worn in the user's pocket 6 or in another portion of the user's clothing. For example, the pump device 100 and the controller device 200 can be attached together and form the pump assembly 10 that comfortably fits into a user's pocket 6. The user can carry the portable infusion pump assembly 10 and use the tube of an infusion set 146 to direct the dispensed medicine to the desired infusion site. Furthermore, a monitoring device 50 can be worn on the user's skin while the pump assembly 10 is carried by the user (e.g., in a pocket). In some embodiments, the bedside infusion pump system 900a may be operable to execute operations according to a closed-loop delivery mode (see FIGS. 5A and 5B) to determine one or more user-specific dosage parameters. The dosage parameters can then be input to the controller device 200 for use in future open-loop and/or closed-loop operations.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
a pump housing configured to receive medicine for dispensation to a user, the pump housing at least partially containing a pump drive system to dispense the medicine through a flow path to the user;
a controller configured to control the pump drive system to dispense the medicine from the pump housing; and
wherein the controller is configured to control the dispensation of the medicine according to a closed-loop delivery mode in which the controller controls the pump drive system to dispense the medicine, receives feedback data in response to the dispensation of the medicine, automatically delivers a corrected dosage of the medicine determined based at least in part on the feedback data, and determines one or more user-specific settings based at least in part on the feedback data and according to an open-loop delivery mode in which one or more insulin dosages for dispensation are based at least in part on the one or more user-specific settings that were determined during the closed-loop delivery mode, wherein said one or more insulin dosages for dispensation during the open-loop delivery mode include a suggested bolus dosage calculated and displayed by the controller during the open-loop delivery mode, wherein the controller determines the suggested bolus dosage during the open-loop delivery mode based at least in part on the one or more user-specific settings of any of the user's insulin sensitivity and the user's carbohydrate ratio, the one or more user-specific settings being determined and stored by the controller during the closed-loop delivery mode.

2. The system of claim 1, wherein the controller is configured to transition from the closed-loop delivery mode to the open-loop delivery mode in response to detecting a transition trigger event.

3. The system of claim 2, wherein the transition trigger event comprises actuation of a user interface button indicating the user's acknowledgement to exit the closed-loop delivery mode.

4. The system of claim 1, wherein the controller determines the suggested bolus dosage according to the function:

Suggested Bolus Dosage=(Food Offsetting Component)+(Blood Glucose Correction Component)−(Insulin Load Correction Component), wherein each of the Food Offsetting Component, the Blood Glucose Correction Component, and the Insulin Load Correction Component are dependent upon one of the one or more user-specific settings that were determined during the closed-loop delivery mode.

5. The system of claim 1, wherein the controller comprises a user interface including a display device and a plurality of user-actuatable buttons.

6. The system of claim 5, wherein the controller comprises a controller housing configured to removably attach to the pump housing.

7. The system of claim 6, wherein the controller is electrically connected to the pump drive system when the controller housing is removably attached to the pump housing.

8. The system of claim 7, wherein the controller is a reusable device and the pump housing and pump drive system are disposable and nonreusable.

9. The system of claim 1, wherein the one or more user-specific settings that were determined during the closed-loop delivery mode comprise values for the user's personal dosage parameters.

10. The system of claim 1, further comprising a monitoring device configured to communicate glucose information to the controller, the glucose information being indicative of a blood glucose level of the user.

11. A portable insulin pump system, comprising:
a disposable and non-reusable pump device including:
a pump housing that defines a space to receive an insulin cartridge; and
a drive system to dispense insulin when the insulin cartridge is received by the pump housing, the drive system including a piston rod that is incrementally movable to apply a dispensing force; and a removable controller device including:
- a controller housing configured to removably attach to the pump housing to provide an electrical connection between the controller device and the pump device;
- control circuitry arranged in the controller housing to electrically communicate with the drive system in the pump housing;
- a user interface connected to the control circuitry, the user interface including a display and one or more user-selectable buttons; and
- a wireless communication device to receive glucose information from a wearable monitoring device, the glucose information being indicative of a blood glucose level of the user, wherein the removable controller device is configured to control dispensation of medicine to a user according to a closed-loop delivery mode in which the controller controls the drive system to dispense the medicine, receives feedback data in response to the dispensation of the medicine, automatically delivers a corrected dosage of the medicine determined based at least in part on the feedback data, and determines customized dosage parameters that are specific to the user based at least in part on the feedback data and according to an open-loop delivery mode in which insulin dosages for dispensation to the user are based at least in part on the customized dosage parameters that were determined during the closed-loop delivery mode, wherein the insulin dosages include a suggested bolus dosage calculated during the open-loop delivery mode, wherein the customized dosage parameters include a customized insulin sensitivity and a customized carbohydrate ratio that are used in the open-loop delivery mode to determine the suggested bolus dosage.

\* \* \* \* \*